(12) United States Patent
McIvor et al.

(10) Patent No.: US 9,827,295 B2
(45) Date of Patent: Nov. 28, 2017

(54) METHODS TO TREAT MUCOPOLYSACCHARIDE TYPE I OR DEFICIENCY IN ALPHA-L-IDURONIDASE USING A RECOMBINANT ADENO-ASSOCIATED VIRUS ENCODING ALPHA-L-IDURONIDASE

(71) Applicants: Regents of the University of Minnesota, Minneapolis, MN (US); REGENXBIO Inc., Rockville, MD (US)

(72) Inventors: R. Scott McIvor, St. Louis Park, MN (US); Lalitha R. Belur, St. Paul, MN (US); Walter Low, Shorewood, MN (US); Carolyn Fairbanks, St. Paul, MN (US); Karen Kozarsky, Bala Cynwyd, PA (US)

(73) Assignees: Regents of the University of Minnesota, Minneapolis, MN (US); REGENXBIO Inc., Rockville, MD (US)

( * ) Notice: Subject to any disclaimer, the term of this patent is extended or adjusted under 35 U.S.C. 154(b) by 0 days.

(21) Appl. No.: 14/889,750

(22) PCT Filed: May 15, 2014

(86) PCT No.: PCT/US2014/038209
§ 371 (c)(1),
(2) Date: Nov. 6, 2015

(87) PCT Pub. No.: WO2014/186579
PCT Pub. Date: Nov. 20, 2014

(65) Prior Publication Data
US 2016/0120960 A1 May 5, 2016

Related U.S. Application Data

(60) Provisional application No. 61/823,757, filed on May 15, 2013.

(51) Int. Cl.
| | | |
|---|---|---|
| *A61K 48/00* | (2006.01) | |
| *C12N 15/86* | (2006.01) | |
| *C12N 15/11* | (2006.01) | |
| *C12N 15/113* | (2010.01) | |
| *C12N 15/00* | (2006.01) | |
| *C12N 15/09* | (2006.01) | |
| *C12N 15/10* | (2006.01) | |
| *A61K 38/47* | (2006.01) | |
| *C12N 7/00* | (2006.01) | |

(52) U.S. Cl.
CPC .............. *A61K 38/47* (2013.01); *C12N 7/00* (2013.01); *C12N 15/86* (2013.01); *A61K 48/00* (2013.01); *C12N 2750/14143* (2013.01); *C12N 2750/14171* (2013.01); *C12N 2830/007* (2013.01); *C12Y 302/01076* (2013.01)

(58) Field of Classification Search
CPC .... A61K 9/0085; A61K 9/0019; A61K 35/76; A61K 35/761; A61K 48/00; C12Y 301/06013; C12Y 302/0105; C12Y 302/01045; C12Y 302/01076; C12Y 310/01001; C12N 15/86
See application file for complete search history.

(56) References Cited

U.S. PATENT DOCUMENTS

| | | |
|---|---|---|
| 5,624,898 A | 4/1997 | Frey, II |
| 6,180,603 B1 | 1/2001 | Frey, II |
| 6,190,659 B1 | 2/2001 | Pancholi et al. |
| 6,309,634 B1 | 10/2001 | Bankiewicz et al. |
| 6,313,093 B1 | 11/2001 | Frey, II |
| 6,342,478 B1 | 1/2002 | Frey, II |
| 6,407,061 B1 | 6/2002 | Frey, II |
| 6,569,661 B1 | 5/2003 | Qin et al. |
| 6,858,206 B2 | 2/2005 | Kakkis |
| 6,953,575 B2 | 10/2005 | Bankiewicz et al. |
| 6,991,785 B2 | 1/2006 | Frey, II |
| 7,084,126 B1 | 8/2006 | Frey, II et al. |
| 7,592,321 B2 * | 9/2009 | Whitley .................. C12N 9/16 424/93.1 |
| 7,989,502 B2 | 8/2011 | Greco et al. |
| 8,153,604 B2 | 4/2012 | Deen et al. |
| 8,252,745 B2 | 8/2012 | Yeomans et al. |
| 8,283,160 B2 | 10/2012 | Frey, II et al. |
| 8,501,691 B2 | 8/2013 | Yeomans et al. |

(Continued)

FOREIGN PATENT DOCUMENTS

| | | |
|---|---|---|
| EP | 1915986 A1 | 4/2008 |
| WO | WO-91/07947 A1 | 6/1991 |

(Continued)

OTHER PUBLICATIONS

Samaranch et al. Hum. Gene Ther. 2012; 23:382-389.*
"U.S. Appl. No. 12/463,575, Response filed Dec. 10, 2012 to Restriction Requirement dated Nov. 9, 2012", 6 pgs.
"U.S. Appl. No. 13/465,575, Response filed May 9, 2013 to Non Final Office Action dated Feb. 11, 2013", 9 pgs.
"U.S. Appl. No. 13/465,575, Non Final Office Action dated Feb. 11, 2013", 15 pgs.
"U.S. Appl. No. 13/465,575, Notice of Allowance dated Aug. 8, 2013", 11 pgs.
"U.S. Appl. No. 13/465,575, Restriction Requirement dated Nov. 9, 2012", 8 pgs.
"U.S. Appl. No. 14/103,597, Examiner Interview Summary dated Dec. 4, 2015", 2 pgs.
"U.S. Appl. No. 14/103,597, Final Office Action dated Jun. 25, 2015", 11 pgs.

(Continued)

*Primary Examiner* — Chang-Yu Wang
(74) *Attorney, Agent, or Firm* — Schwegman Lundberg & Woessner, P.A.

(57) ABSTRACT

A method to prevent, inhibit or treat one or more symptoms associated with a disease of the central nervous system by intrathecally, intracerebroventricularly or endovascularly administering a rAAV encoding a gene product associated with the disease, e.g., a mammal in which the gene product is absent or present at a reduced level relative to a mammal without the disease.

26 Claims, 20 Drawing Sheets

(56) References Cited

U.S. PATENT DOCUMENTS

| | | | | |
|---|---|---|---|---|
| 8,545,837 B2* | 10/2013 | Zhu | ............... | A61K 9/0085 |
| | | | | 424/94.3 |
| 8,609,088 B2* | 12/2013 | Wolf | ............... | A61K 38/46 |
| | | | | 424/94.61 |
| 8,622,993 B2 | 1/2014 | Frey, II et al. | | |
| 8,715,661 B2* | 5/2014 | Pardridge | ............... | C07K 16/2869 |
| | | | | 424/134.1 |
| 8,796,236 B2* | 8/2014 | Dodge | ............... | C12N 15/86 |
| | | | | 424/93.2 |
| 8,920,801 B2* | 12/2014 | Pardridge | ............... | C07K 16/2869 |
| | | | | 424/134.1 |
| 8,999,948 B2* | 4/2015 | Tubert | ............... | C12N 9/14 |
| | | | | 435/320.1 |
| 9,102,949 B2* | 8/2015 | Gao | ............... | C12N 15/86 |
| 9,133,482 B2* | 9/2015 | Harper | ............... | C12N 15/113 |
| 9,220,677 B2* | 12/2015 | Zhu | ............... | A61K 9/0085 |
| 9,249,424 B2* | 2/2016 | Wolf | | |
| 9,265,843 B2* | 2/2016 | During | ............... | A61K 48/005 |
| 9,279,132 B2* | 3/2016 | Bosch Tubert | ............... | C12N 9/14 |
| 9,283,181 B2* | 3/2016 | Calias | ............... | A61K 9/0085 |
| 9,320,711 B2* | 4/2016 | Natoli | ............... | A61K 9/0085 |
| 9,415,121 B2* | 8/2016 | Kaspar | ............... | A61K 48/0075 |
| 9,469,851 B2* | 10/2016 | Harper | ............... | C12N 15/113 |
| 2001/0043915 A1 | 11/2001 | Frey, II | | |
| 2002/0072498 A1 | 6/2002 | Frey, II | | |
| 2002/0082215 A1 | 6/2002 | Frey, II | | |
| 2002/0169102 A1 | 11/2002 | Frey, II | | |
| 2003/0072793 A1 | 4/2003 | Frey, II et al. | | |
| 2003/0165434 A1 | 9/2003 | Reinhard et al. | | |
| 2003/0215398 A1 | 11/2003 | Frey, II | | |
| 2003/0219414 A1* | 11/2003 | Podsakoff | ............... | C12N 15/86 |
| | | | | 424/93.2 |
| 2004/0204379 A1 | 10/2004 | Cheng et al. | | |
| 2006/0057114 A1* | 3/2006 | Whitley | ............... | C12N 9/16 |
| | | | | 424/93.2 |
| 2006/0188496 A1 | 8/2006 | Bentz et al. | | |
| 2006/0216317 A1 | 9/2006 | Reinhard et al. | | |
| 2007/0092500 A1 | 4/2007 | Frey, II et al. | | |
| 2008/0305077 A1 | 12/2008 | Frey, II et al. | | |
| 2009/0068155 A1 | 3/2009 | Frey, II et al. | | |
| 2009/0117156 A1* | 5/2009 | Passini | ............... | A61K 48/0083 |
| | | | | 424/233.1 |
| 2009/0136505 A1 | 5/2009 | Bentz et al. | | |
| 2009/0264506 A1 | 10/2009 | Reinhard et al. | | |
| 2010/0061959 A1 | 3/2010 | Frey, II et al. | | |
| 2010/0068183 A1* | 3/2010 | Whitley | ............... | C12N 9/16 |
| | | | | 424/93.2 |
| 2010/0173979 A1* | 7/2010 | Dodge | ............... | C12N 15/86 |
| | | | | 514/44 R |
| 2010/0199366 A1* | 8/2010 | Cooper | ............... | C12N 15/8509 |
| | | | | 800/14 |
| 2011/0070241 A1* | 3/2011 | Yang | ............... | A61K 39/395 |
| | | | | 424/158.1 |
| 2011/0288160 A1* | 11/2011 | During | ............... | A61K 48/005 |
| | | | | 514/44 R |
| 2012/0177605 A1* | 7/2012 | Kaspar | ............... | A61K 48/005 |
| | | | | 424/93.2 |
| 2012/0288489 A1* | 11/2012 | Wolf | ............... | A61K 38/46 |
| | | | | 424/94.61 |
| 2013/0039888 A1* | 2/2013 | McCarty | ............... | C12N 9/14 |
| | | | | 424/93.2 |
| 2013/0096488 A1 | 4/2013 | Frey, II | | |
| 2013/0195801 A1* | 8/2013 | Gao | ............... | C12N 15/86 |
| | | | | 424/93.2 |
| 2013/0225666 A1* | 8/2013 | Kaspar | ............... | A61K 48/0075 |
| | | | | 514/44 R |
| 2013/0323207 A1* | 12/2013 | McCarty | ............... | C12N 9/14 |
| | | | | 424/93.2 |
| 2014/0045925 A1* | 2/2014 | Harper | ............... | C12N 15/113 |
| | | | | 514/44 R |
| 2014/0088179 A1 | 3/2014 | Davidson | | |
| 2014/0171491 A1* | 6/2014 | Wolf | ............... | A61K 38/46 |
| | | | | 514/44 R |
| 2014/0219974 A1* | 8/2014 | Pan | ............... | A61K 48/0075 |
| | | | | 424/93.21 |
| 2014/0322169 A1* | 10/2014 | Harper | ............... | C12N 15/113 |
| | | | | 424/93.2 |
| 2014/0335054 A1* | 11/2014 | Gao | ............... | C12N 15/86 |
| | | | | 424/93.2 |
| 2015/0210771 A1* | 7/2015 | Crystal | ............... | C07K 16/22 |
| | | | | 514/44 R |
| 2016/0038613 A1* | 2/2016 | Kaspar | ............... | A61K 48/0075 |
| | | | | 514/44 R |
| 2016/0076028 A1* | 3/2016 | Flanigan | ............... | A61K 48/005 |
| | | | | 424/93.2 |
| 2016/0175406 A1* | 6/2016 | McCarty | ............... | C12N 9/14 |
| | | | | 424/93.2 |
| 2016/0272976 A1* | 9/2016 | Kaspar | ............... | C12N 9/0089 |
| 2016/0310548 A1* | 10/2016 | Harper | ............... | C07K 14/4707 |
| 2017/0029849 A1* | 2/2017 | Harper | ............... | C12N 15/113 |

FOREIGN PATENT DOCUMENTS

| | | | | |
|---|---|---|---|---|
| WO | WO 9906562 A1 * | 2/1999 | ........ | A61K 38/1816 |
| WO | WO-9906562 A1 | 2/1999 | | |
| WO | WO-00/33813 A2 | 6/2000 | | |
| WO | WO-00/33814 A2 | 6/2000 | | |
| WO | WO-01/41782 A2 | 6/2001 | | |
| WO | WO-02/32449 A2 | 4/2002 | | |
| WO | WO-02/086105 A1 | 10/2002 | | |
| WO | WO-03/072056 A2 | 9/2003 | | |
| WO | WO-2008/049588 A1 | 5/2008 | | |
| WO | WO-2011/133890 A1 | 10/2011 | | |
| WO | WO-2014186579 A1 | 11/2014 | | |
| WO | WO-2015013148 A2 | 1/2015 | | |
| WO | WO-2016187017 A1 | 11/2016 | | |

OTHER PUBLICATIONS

"U.S. Appl. No. 14/103,597, Non Final Office Action dated Jan. 5, 2015", 12 pgs.

"U.S. Appl. No. 14/103,597, Notice of Allowance dated Sep. 11, 2015", 9 pgs.

"U.S. Appl. No. 14/103,597, Notice of Allowance dated Oct. 7, 2015", 5 pgs.

"U.S. Appl. No. 14/103,597, Preliminary Amendment filed Dec. 12, 2013", 6 pgs.

"U.S. Appl. No. 14/103,597, Response filed Apr. 6, 2015 to Non Final Office Action dated Jan. 5, 2015", 13 pgs.

"U.S. Appl. No. 14/103,597, Response filed Aug. 25, 2015 to Final Office Action dated Jun. 25, 2015", 7 pgs.

"U.S. Appl. No. 14/103,597, Response filed Nov. 25, 2014 to Restriction Requirement dated Sep. 25, 2014", 6 pgs.

"U.S. Appl. No. 14/103,597, Restriction Requirement dated Sep. 25, 2014", 8 pgs.

"European Application Serial No. 14798331.6, Office Action dated Jan. 19, 2016", 2 pgs.

"International Application Serial No. PCT/US2014/038209, International Preliminary Report on Patentability dated Nov. 26, 2015", 7 pgs.

"Russian Application Serial No. 2015152546, Office Action dated Feb. 11, 2016", (w/ English Translation), 3 pgs.

"Russian Application Serial No. 2015152546, Response filed May 11, 2016 to Office Action dated Feb. 11, 2016", (w/ English Translation of Claims), 31 pgs.

Barone, R., et al., "Extraneurologic Symptoms as Presenting Signs of Sanfilippo Disease", *Pediatr Neurol.*, 25(3), (Sep. 2001), 254-7.

Cherin, P., et al., "[Neurological manifestations of type 1 Gaucher's disease: Is a revision of disease classification needed?]", *Rev Neurol (Paris)*, 162(11), [Article in French, w/ English Summary], (Nov. 2006), 1076-83.

Dhuria, S. V, et al., "Intranasal delivery to the central nervous system: mechanisms and experimental considerations", *J Pharm Sci.*, 99(4), (Apr. 2010), 1654-73.

Donovan, M. D., et al., "Large molecule and particulate uptake in the nasal cavity: the effect of size on nasal absorption", *Advanced Drug Delivery Reviews*, vol. 29, (1998), 147-155.

(56) References Cited

OTHER PUBLICATIONS

Draghia, R., et al., "Gene delivery into the central nervous system by nasal instillation in rats", *Gene Therapy*, 2(6), (1995), 418-423.

Han, I. K., et al., "Enhanced brain targeting efficiency of intranasally administered plasmid DNA: an alternative route for brain gene therapy", *J. Mol. Med. (Berl)*, 85(1), (2006), 75-83.

Hoffmann, B., et al., "Neurological manifestations in lysosomal storage disorders—from pathology to first therapeutic possibilities", *Neuropediatrics*, 36(5), Oct. 2005), 285-289.

Jerusalmi, A., et al., "Effect of Intranasal Administration of Semliki Forest Virus Recombinant Particles Expressing Reporter and Cytokine Genes on the Progression of Experimental Autoimmune Encephalomyelitis", *Mol Therapy*, 8(6), (2003), 886-894.

Kaback, M. M, et al., "Hexosaminidase A Deficiency", In: Pagon RA, Bird TD, Dolan CR, et al., editors. GeneReviews™ [Internet]. Seattle (WA): University of Washington, Seattle; 1993—.Available from: http://www.ncbi.nlm.nih.gov/books/NBK1218/, (Mar. 11, 1999 [Updated Aug. 11, 2011]), 13 pgs.

Kaemmerer, William F., et al., "In Vivo Transduction of Cerebellar Purkinje Cells Using Adeno-Associated Virus Vectors", *Molecular Therapy*, 2(5), (2000), 446-457.

Kakkis, E., et al., "Intrathecal enzyme replacement therapy reduces lysosomal storage in the brain and meninges of the canine model of MPS I", *Molecular Genetics and Metabolism*, vol. 83, (2004), 163-174.

Laing, J., "Intranasal administration of the growth compromised HSV-2 vector DeltaRR prevents kainate induced seizures and neuronal loss in rats and mice", *Mol Therapy*, 13(5), (2006), 870-881.

Lemiale, F., et al., "Enhanced Mucosal Immunoglobulin a Response of Intranasal Adenoviral Vector Human Immunodeficiency Virus Vaccine and Localization in the Central Nervous System", *J. Vitol.*, 77(18), (2003), 10078-10087.

Martin, R., et al., "Recognition and diagnosis of mucopolysaccharidosis II (Hunter syndrome).", *Pediatrics*, 121(2), (Feb. 2008), e377-e386.

Martino, S., et al., "Absence of Metabolic Cross-correction in Tay-Sachs Cells", *The Journal of Biological Chemistry*, 277(23), (2002), 20177-20184.

Talegaonkar, S., et al., "Intranasal delivery: An approach to bypass the blood brain barrier", *Indian Journal of Pharmacology*, vol. 36, (2004), 140-147.

Wolf, D. A., et al., "Lysosomal enzyme can bypass the blood-brain barrier and reach the CNS following intranasal administration", *Molecular Genetics and Metabolism*, 106(1), (2012), 131-134.

Zheng, Y., et al., "Treatment of the mouse model of mucopolysaccharidosis I with retrovirally transduced bone marrow", *Molecular Genetics and Metabolism*, 79(4), (2003), 233-244.

"International Application Serial No. PCT/US2014/038209, International Search Report dated Sep. 26, 2014", 3 pgs.

"International Application Serial No. PCT/US2014/038209, Written Opinion dated Sep. 26, 2014", 10 pgs.

Hartung, S. D. et al., "Correction of Metabolic, Craniofacial, and Neurologic Abnormalities in MPS I Mice Treated at Birth with Adeno-associated Virus Vector Transducing the Human A-L-Iduronidase Gene", Molecular Therapy, 9(6), (2004), 866-875.

Janson, Christopher G., et al., "Comparison of Endovascular and Intraventricular Gene Therapy With Adeno-Associated Virus-alpha-L-Iduronidase for Hurler Disease", Neurosurgery, 74(1), (2014), 99-111.

Samaranch, Lluis, et al., "Strong Cortical and Spinal Cord Transduction After AAV7 and AAV9 Delivery into the Cerebrospinal Fluid of Nonhuman Pirimates", Human Gene Therapy, 24, (May 2013), 526-532.

Watson, G., et al., "Intrathecal adminstration of AAV vectors for the treatment of lysosomal storage in the brains of MPS I mice", Gene Therapy, 13,(2006), 1-9.

Wolf, Daniel A., et al., "Direct gene transfer to the CNS prevents emergence of Neurologic disease in a murine model of mucopolysaccharidosis type I", Neurobiology of Disease, 43(1), (2011), 123-133.

"ASGCT—American Society of Gene & Cell Therapy. 16th Annual Meeting 2013, Abstracts", Retrieved from the Internet: URL:http://www.asgct.orgimeetings-educational-programsjasgct-annual-meetingsjarchived-annual-meetings/2013-annual-meetingjat-tendeejabstracts [retrieved on Dec. 2, 2016], (Apr. 19, 2013).

"European Application Serial No. 14798331.6, Extended European Search Report dated Dec. 13, 2016", 12 pgs.

"international Application Serial No. PCT/US2016/032392, International Search Report dated Aug. 19, 2016", 3 pgs.

"International Application Serial No. PCT/US2016/032392, Written Opinion dated Aug. 19, 2016", 5 pgs.

Belur, Let, et al., "AAV Vector-Mediated Iduronidase Gene Delivery in a Murine Model of Mucopolysaccharidosis Type I: Comparing Different Routes of Delivery to the CNS", Abstracts for the ASGCT16th Annual Meeting. May 15-18, 2013. Salt Lake City. Utah, US, Retrieved from the Internet: <URL:http://www.nature.comjmtjjournaljv21/n1s/pdf/mt201382a.pdf> [retrieved on Dec. 2, 2016], (Apr. 19, 2013).

Ciron, C, et al., "Human [alpha]-Iduronidase Gene Transfer Mediated by Adena-Associated Virus Types 1. 2. and 5 in the Brain of Nonhuman Primates: Vector Diffusion and Biodistribution", Human Gene Therapy, vol. 20. No. 4, (Apr. 1, 2009), 350-360.

Fu, et al, "Neurological correction of lysosomal storage in a mucopolysaccharidosis IIIB mouse model by adeno-associated virus-mediated gene delivery", Molecular Therapy, vol. 5, No. 1, (Jan. 1, 2002), 42-49 pgs.

Guo, Yansu, "A single injection of recombinant adeno-associated virus into the lumbar cistern delivers transgene expression throughout the whole spinal cord", HHS Public Access, Author manuscript, Mol Neurobiol., 53(5), (Jul. 2016), 3235-3248.

Iwamoto, N, et al., "Global diffuse distribution in the brain and efficient gene delivery to the dorsal root ganalia by intrathecal injection of adena-associated viral vector serotype 1", Journal of Gene Medicine. John Wiley & Sons, Inc, US, vol. 11, No. 6, (Jun. 1, 2009), 498-505.

Janson, C, et al., "Comparison of intraventricular vs. endovascular AAV5 mediated IDUA gene delivery to the brain in the MPS-I mouse model", Molecular Genetics and Metabolism, vol. 102. No. 2, Amsterdam. N L, (Feb. 1, 2011), S22.

McCarty, D M, et al., "Mannitol-facilitated CNS entry of rAAV2 vector significantly delayed the neurological disease progression in MPS IIIB mice", Gene Therapy, vol. 16, No. 11, (Jul. 9, 2009), 1340-1352.

Vulchanova, L, et al., "Differential adena-associated virus mediated gene transfer to sensory neurons following intrathecal delivery by direct lumbar puncture", Molecular Pain, vol. 6, No. 1, (Jan. 1, 2010), 31.

Wang, Hongyan, et al., "Widespread spinal cord transduction by intrathecal injection of rAAV delivers efficacious RNAi therapy for amyotrophic lateral sclerosis", Human Molecular Genetics, vol. 23, No. 3, (2014), 668-681.

"Australian Application Serial No. 2014255417, First Examination Report dated Jul. 9, 2017", 6 pgs.

"Chinese Application Serial No. 201480027622.1, Office Action dated Jul. 28, 2017", (w/ English Translation), 19 pgs.

"European Application Serial No. 14798331.6, Response filed Jul. 19, 2017 to Extended European Search Report dated Dec. 13, 2016", 10 pgs.

\* cited by examiner

*All expts. carried out in adult MPS I (IDUA deficient) mice*

| Route of Adm. | Mice | CP | Age at inj. | Sacrificed |
|---|---|---|---|---|
| 1. ICV | Immunodeficient | No | 4.5 mths | 10 wks post inj. |
| 2. ICV | Immunocompetent | Yes | 4.5 mths | 8 wks post inj. |
| 3. Intrathecal | Immunocompetent | Yes | 4.5 mths | 11 wks post inj. |
| 4. ICV | Immunotolerized | No | 3 mths | 9 wks post inj. |

*All animals injected with 10 ul AAV9 vector ($3 \times 10^{11}$ particles)*

ICV injections: Right lateral ventricle
IT injections: Lumbar area

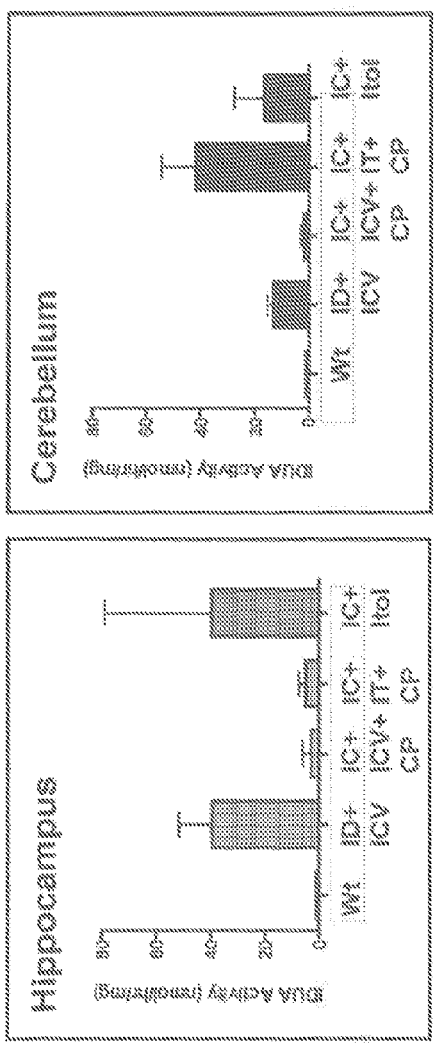
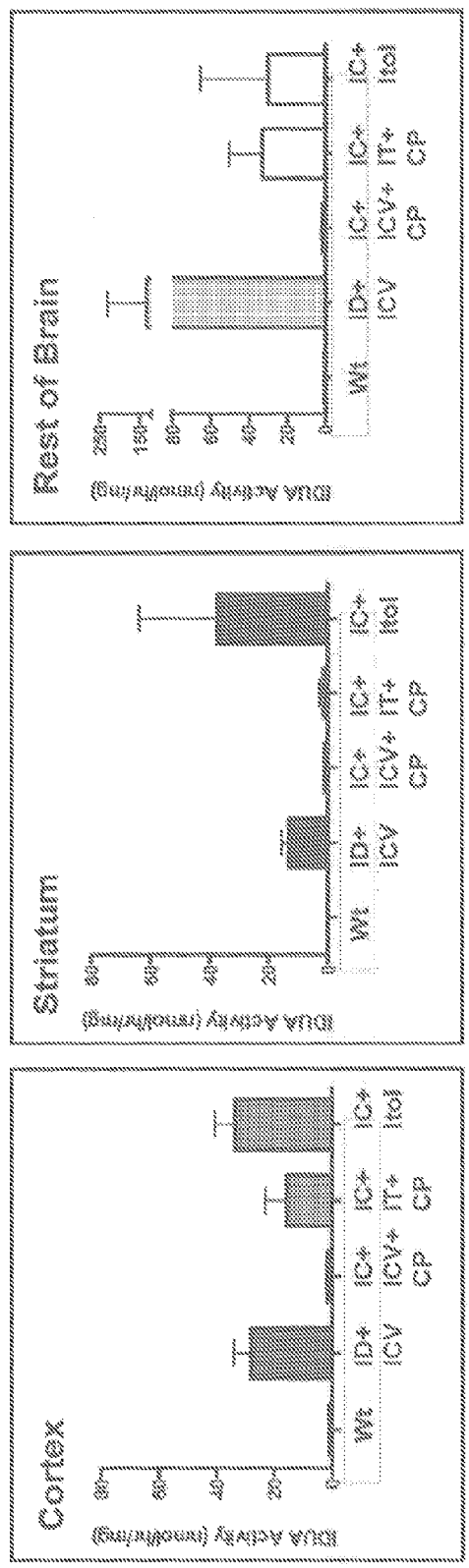
FIG. 7

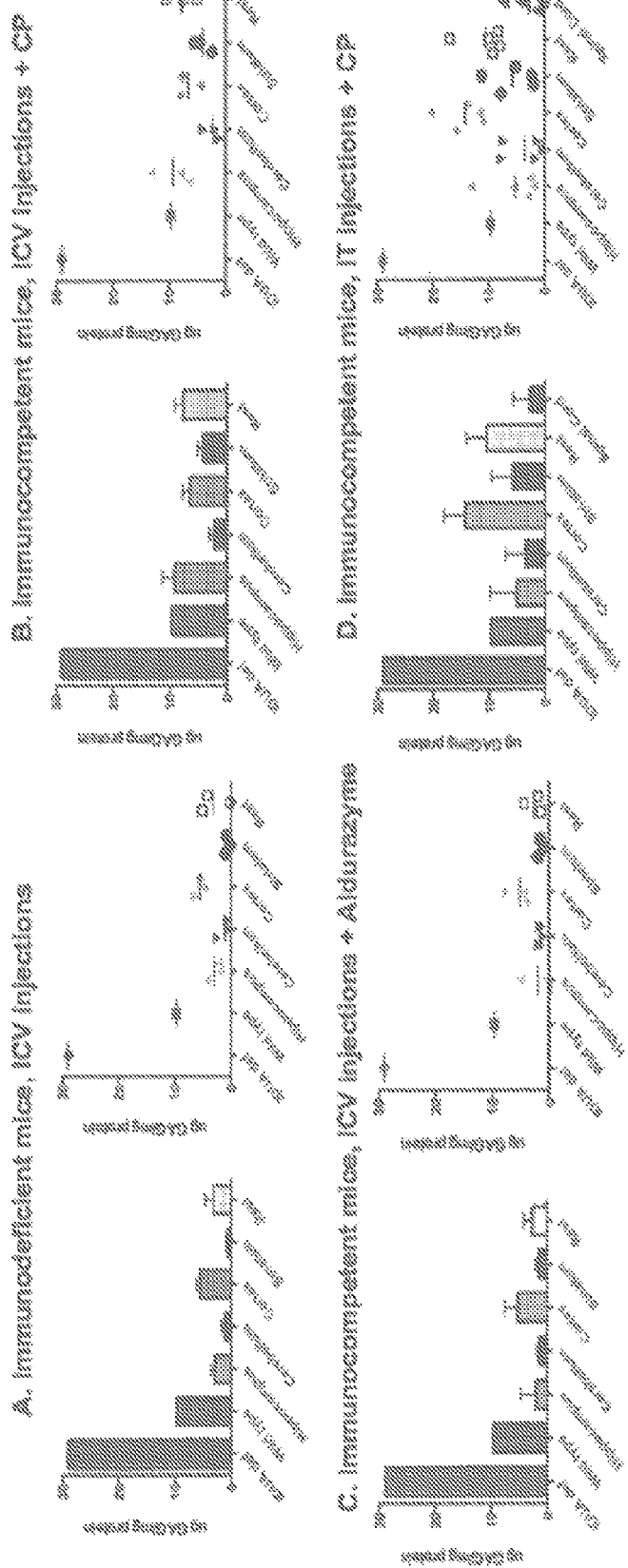

Figure 9. Experimental design

| Route of Vector administration | Immune competency | Immune modulation | Age of animals at injection | Expt. end point (post-injection) |
|---|---|---|---|---|
| ICV | Immunodeficient | None | | 10 weeks |
| ICV | Immunocompetent | Immunosuppression w/CP (partial regimen) | 4.5 months | 8 weeks |
| ICV | Immunocompetent | Immunotolerization | 4.5 months | 11 weeks |
| ICV | Immunocompetent | None | 3 months | |
| ICV | Immunocompetent | Immunosuppression w/CP (full regimen) | 3 months | |
| IT | Immunocompetent | Immunosuppression w/CP (full regimen) | 3 months | 9 weeks |
| IT | Immunocompetent | Enzyme tolerization | 4.5 months | 10 weeks |
| IT | Immunocompetent | None | 4.5 months | 11 weeks |

Abbreviations:
ICV: Intracerebroventricular
IT: Intrathecal
CP: Cyclophosphamide Expts. were carried out in adult MPS I (IDUA deficient) mice
All animals were injected with 10 µL AAV9_vector ($3 \times 10^{11}$ particles)

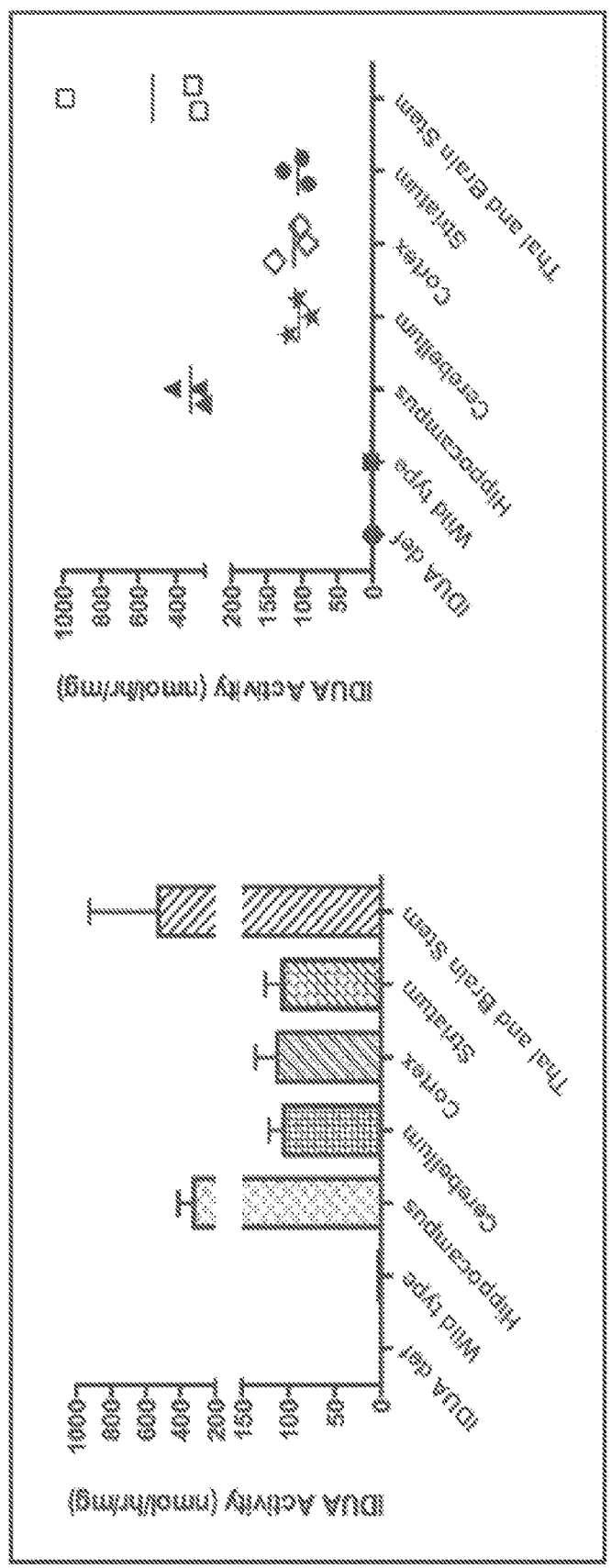
Figure 10. Intracranial Delivery into Immunodeficient Animals

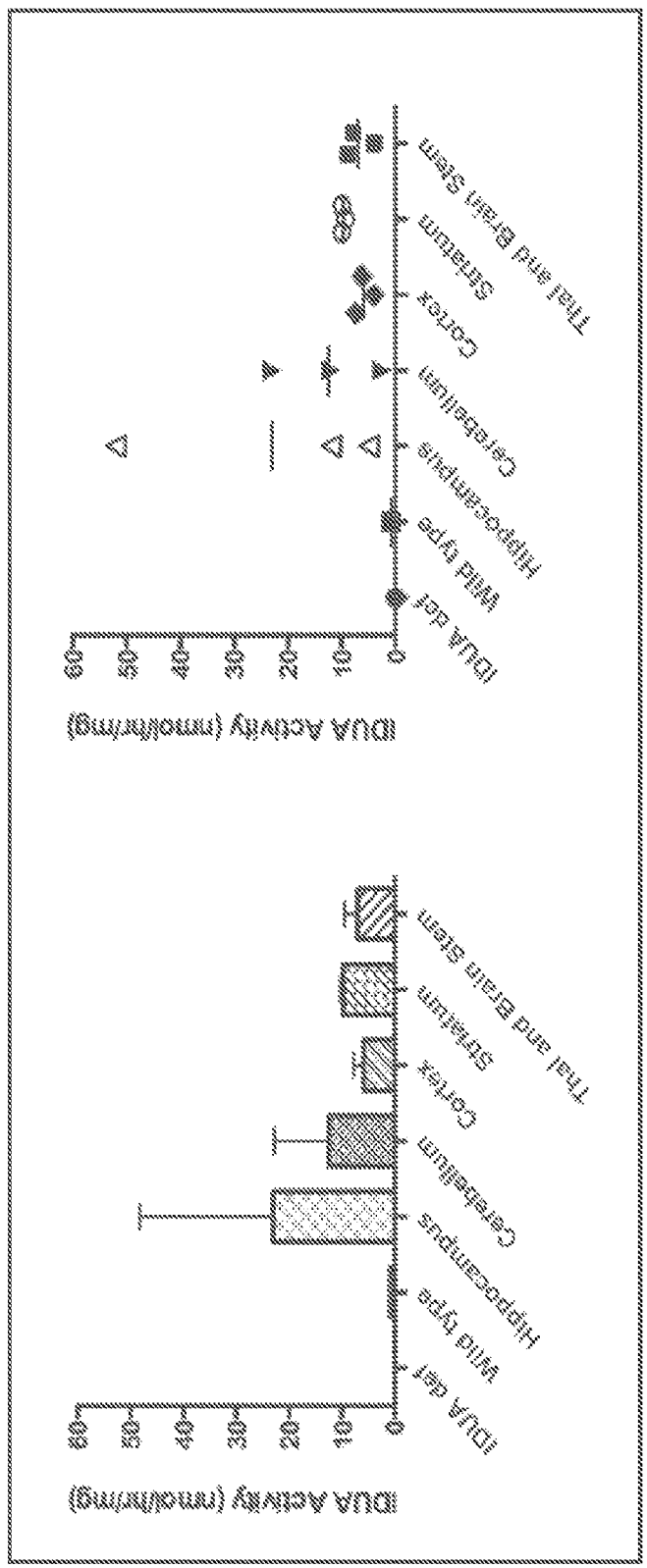
Figure 11. Intracranial Delivery into Immunocompetent mice + Immunosuppression with Cyclophosphamide

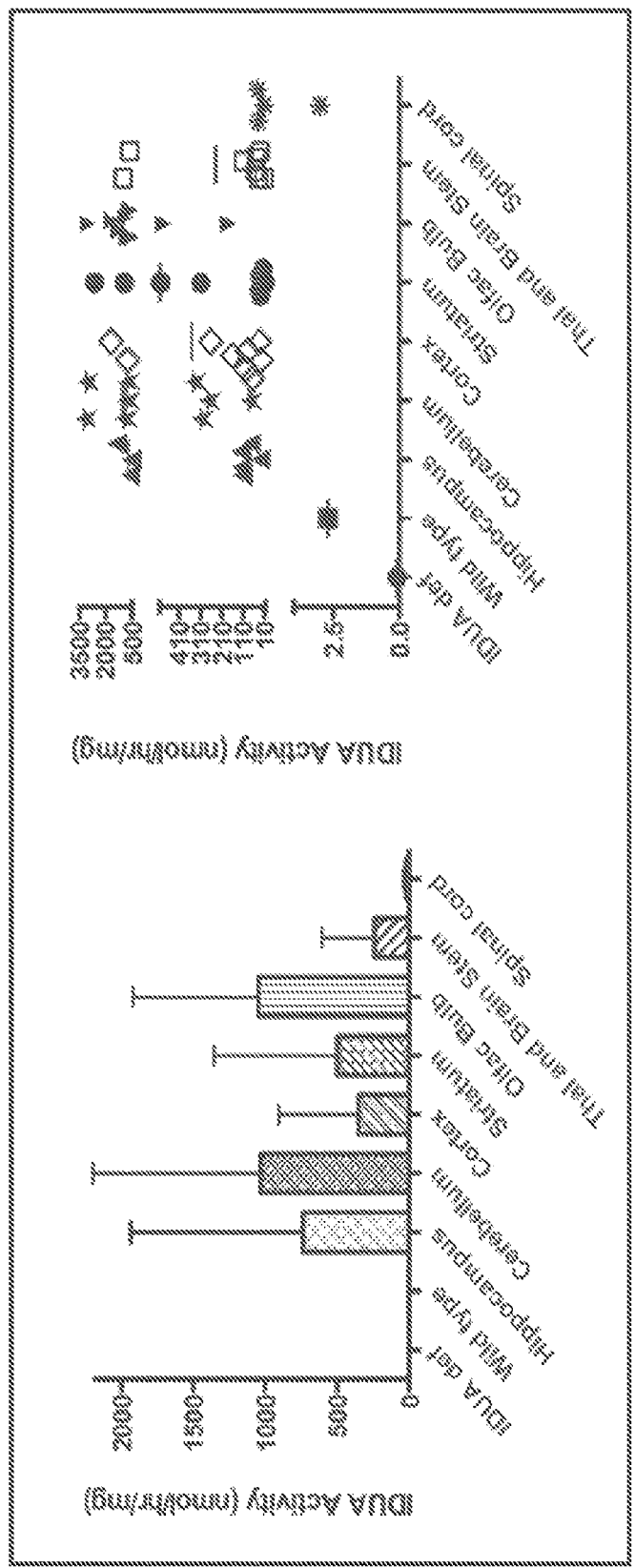
Figure 12. Intracranial Delivery to Immunocompetent mice + Immunotolerization with Aldurazyme

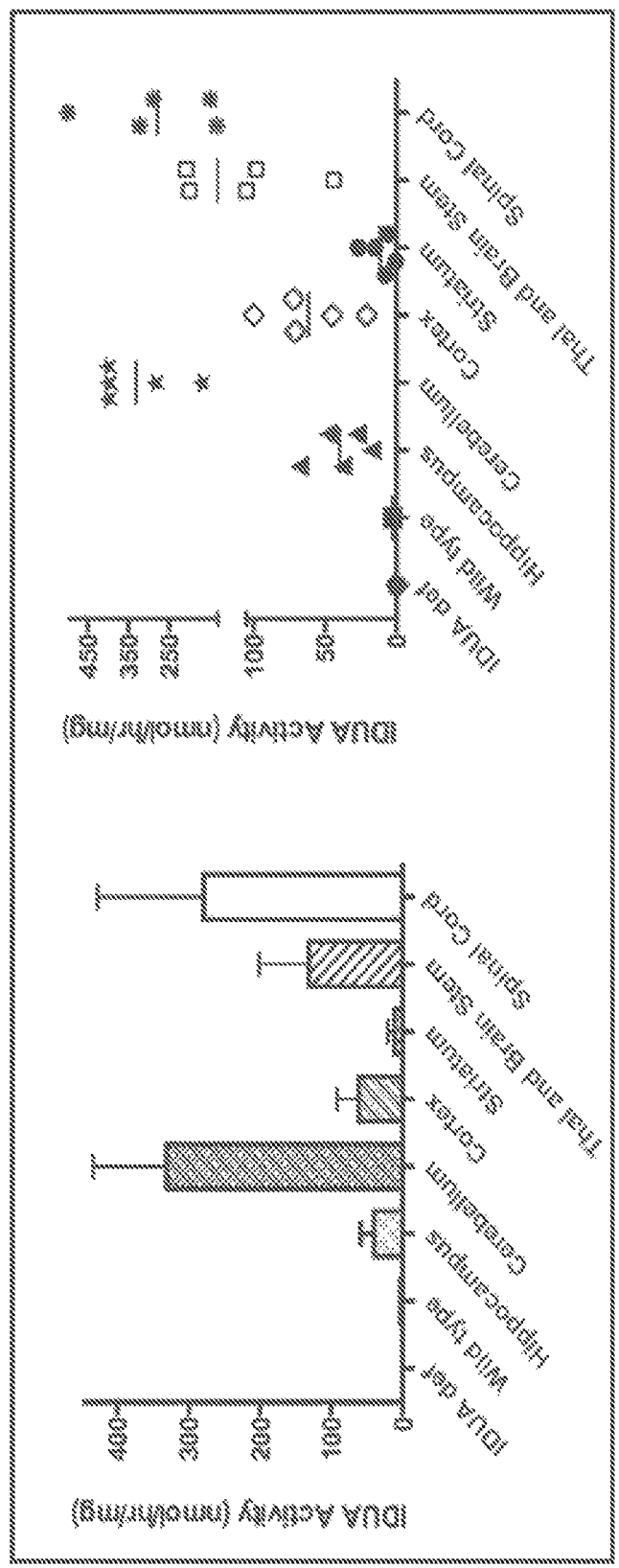
Figure 13. Intrathecal Delivery to Immunocompetent Mice + Immunosuppression with Cyclophosphamide

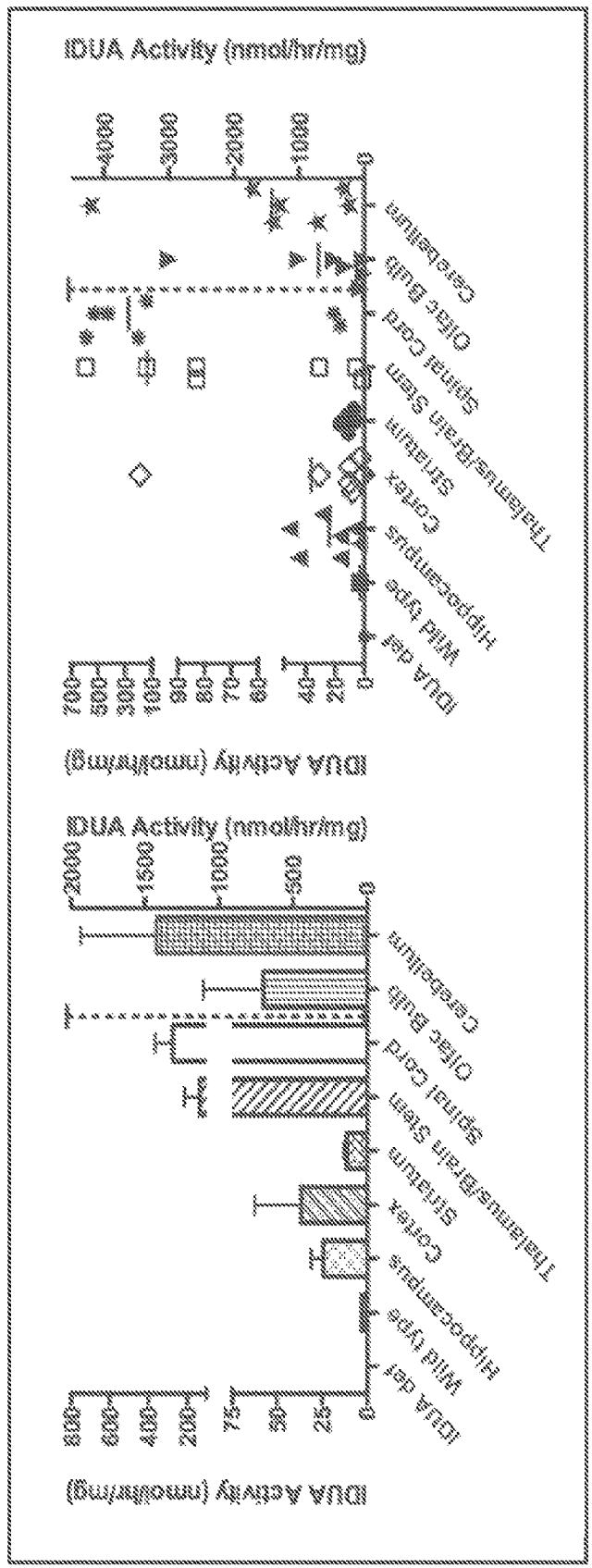
Figure 14. Intrathecal Delivery to Immunocompetent Mice + Immunotolerization with Aldurazyme

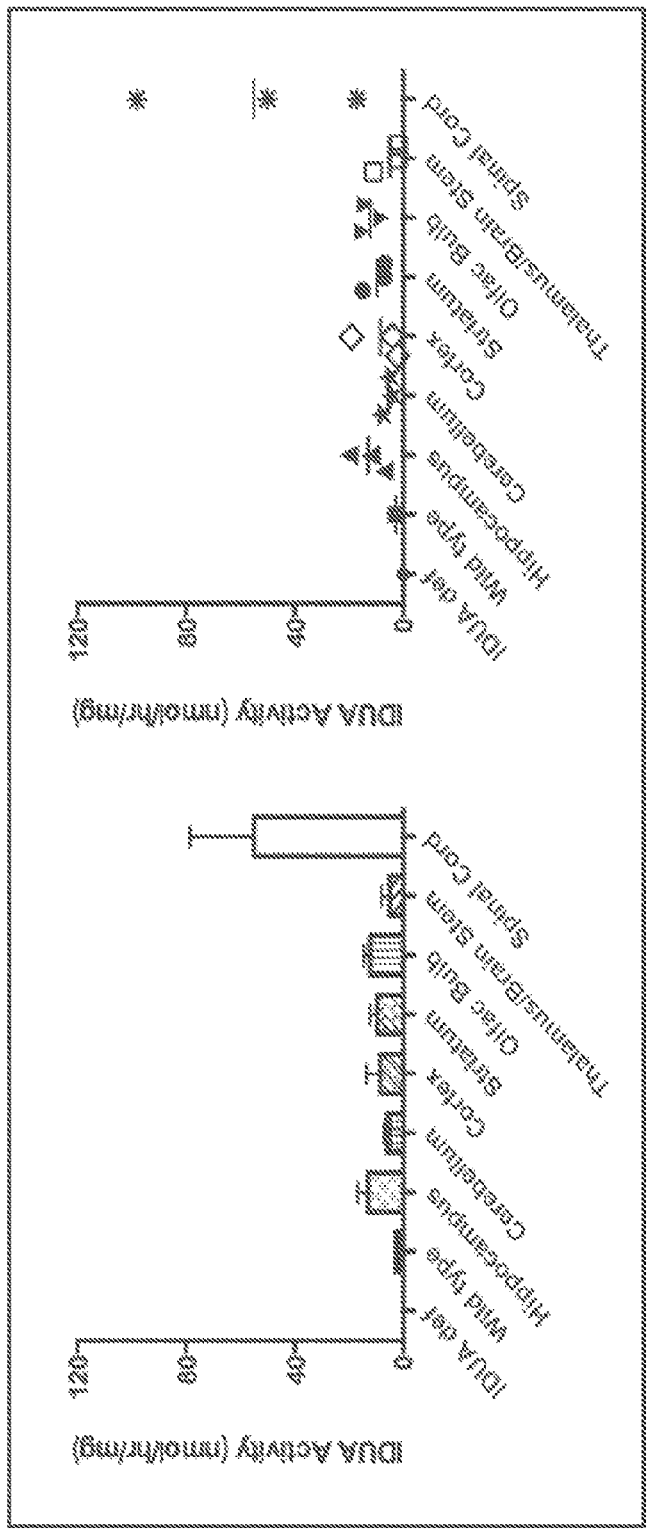
Figure 15. Intrathecal Delivery to Immunocompetent Animals (Controls-No Immunosuppression, No Immunotolerization)

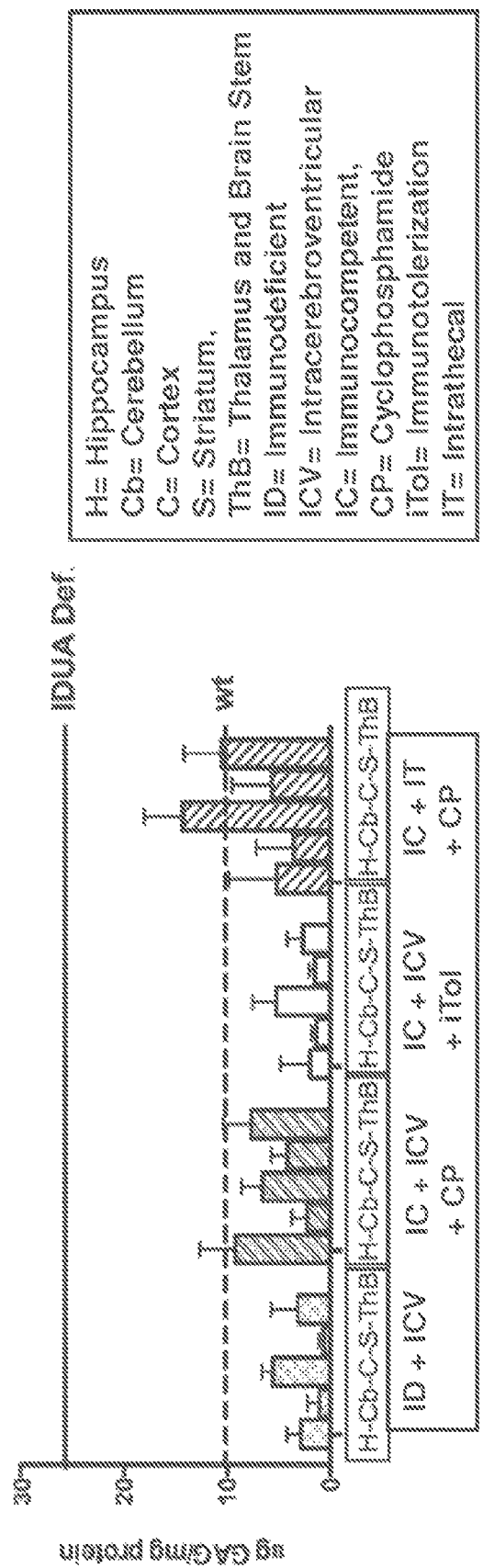
Figure 16. Normalization of Glycosaminoglycans after Intracranial or Intrathecal Administration of AAV9-IDUA

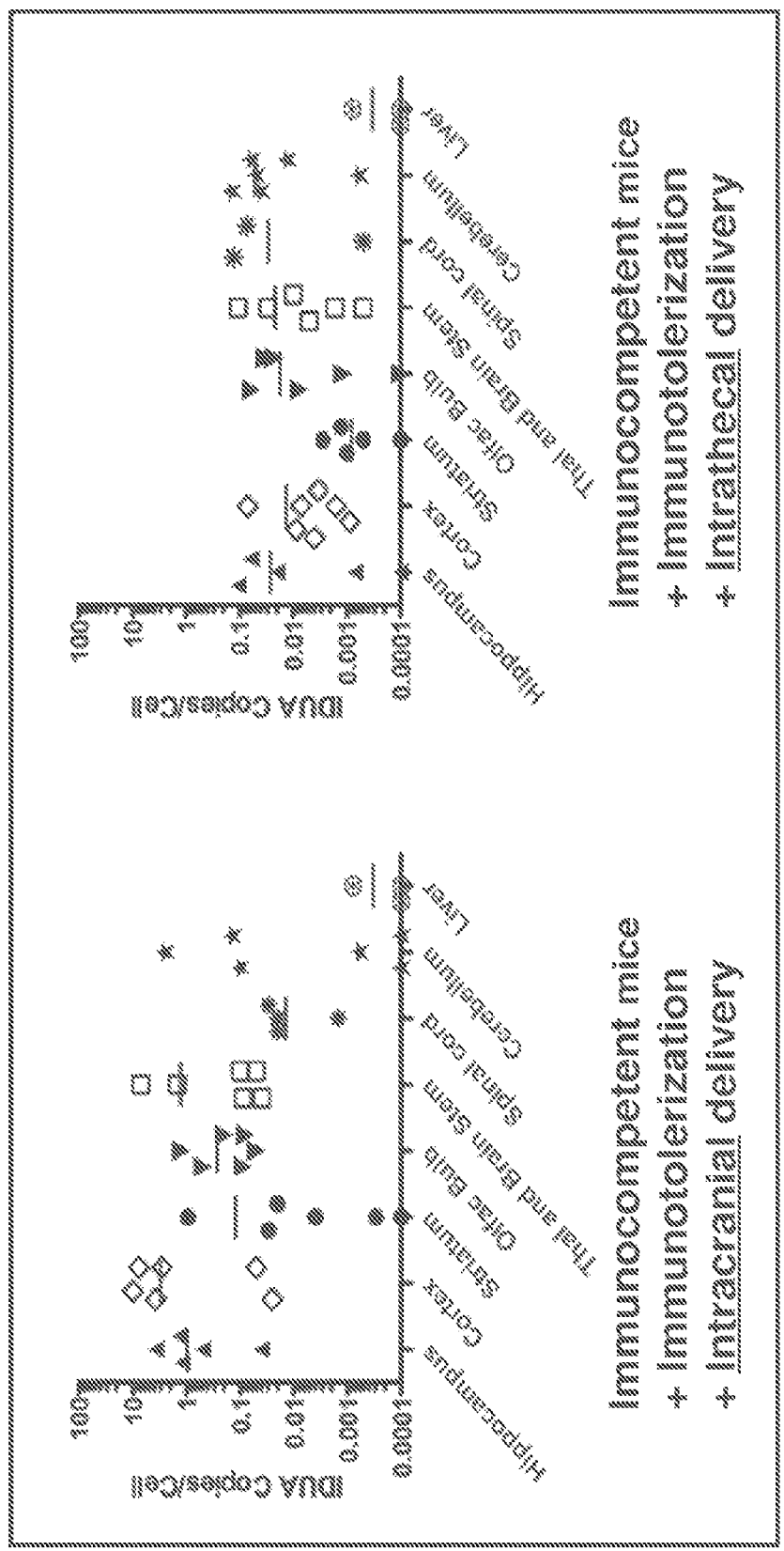

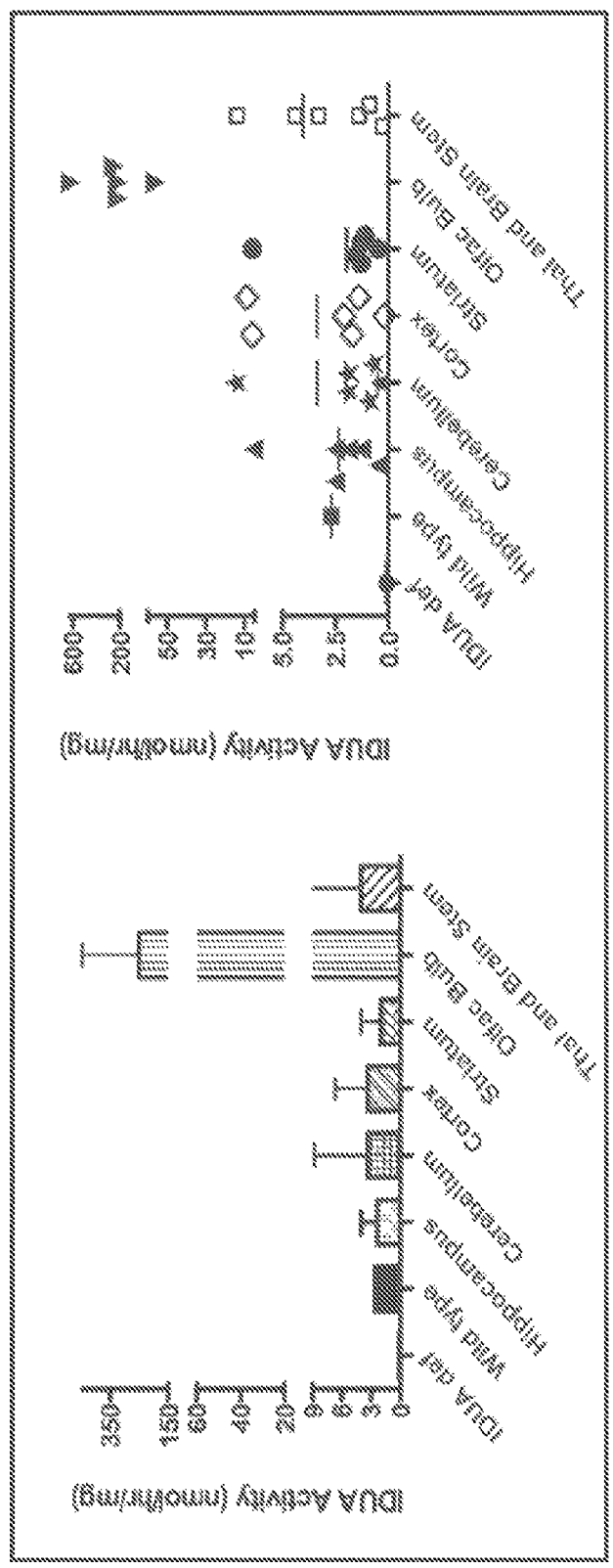
Figure 19. Intranasal Delivery to Immunocompetent Animals + Immunosuppression with Cyclophosphamide

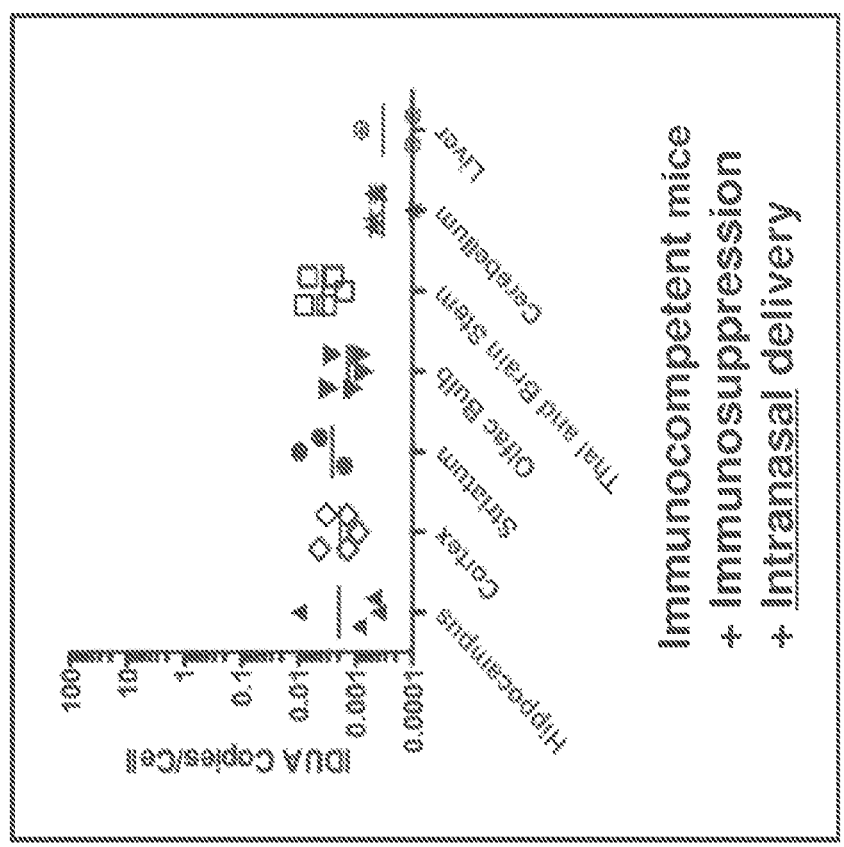

METHODS TO TREAT MUCOPOLYSACCHARIDE TYPE I OR DEFICIENCY IN ALPHA-L-IDURONIDASE USING A RECOMBINANT ADENO-ASSOCIATED VIRUS ENCODING ALPHA-L-IDURONIDASE

CROSS-REFERENCE TO RELATED APPLICATIONS

This application is a U.S. National Stage filing under 35 U.S.C. 371 from International Application No. PCT/US2014/038209, filed on May 15, 2014 and published as WO 2014/186579A1 on 20 Nov. 2014, which claims the benefit of the filing date of U.S. application Ser. No. 61/823,757, filed on May 15, 2013, the disclosures of which are incorporated by reference herein.

STATEMENT OF GOVERNMENT RIGHTS

This invention was made with government support under HD032652 and DK094538 awarded by the National Institutes of Health. The government has certain rights in the invention.

BACKGROUND

The mucopolysaccharidoses (MPSs) are a group of 11 storage diseases caused by disruptions in glycosaminoglycan (GAG) catabolism, leading to their accumulation in lysosomes (Muenzer, 2004; Munoz-Rojas et al., 2008). Manifestations of varying severity include organomegaly, skeletal dysplasias, cardiac and pulmonary obstruction and neurological deterioration. For MPS I, deficiency of iduronidase (IDUA), severity ranges from mild (Scheie syndrome) to moderate (Hurler-Scheie) to severe (Hurler syndrome), with the latter resulting in neurologic deficiency and death by age 15 (Muenzer, 2004; Munoz-Rojas et al., 2008). Therapies for MPSs have been for the most part palliative. However, there are some of the MPS diseases, including Hurler syndrome, for which allogeneic hematopoietic stem cell transplantation (HSCT) has exhibited efficacy (Krivit, 2004; Orchard et al., 2007; Peters et al., 2003). Additionally, for more and more of the MPS diseases, enzyme replacement therapy (ERT) is becoming available (Brady, 2006). In general, HSCT and ERT result in the clearing of storage materials and improved peripheral conditions, although some problems persist after treatment (skeletal, cardiac, corneal clouding). The primary challenge in these cellular and enzyme therapies is effectiveness in addressing neurological manifestations, as peripherally administered enzyme does not penetrate the blood-brain barrier and HSCT has been found to be of benefit for some, but not all, MPS's.

MPS I has been one of the most extensively studied of the MPS diseases for development of cellular and molecular therapies. The effectiveness of allogeneic HSCT is most likely the result of metabolic cross-correction, whereby the missing enzyme is released from donor-derived cells and subsequently taken up by host cells and trafficked to lysosomes, where the enzyme contributes to lysosomal metabolism (Fratantoni et al., 1968). Clearing of GAG storage materials is subsequently observed in peripheral organs such as liver and spleen, there is relief from cardiopulmonary obstruction and improvement in corneal clouding (Orchard et al., 2007). Of particular importance is the effect of allogeneic stem cell transplantation on the emergence of neurologic manifestations in the MPS diseases. In this regard, there is evidence for several MPS diseases that individuals engrafted with allogeneic stem cells face an improved outcome in comparison with untransplanted patients (Bjoraker et al., 2006; Krivit, 2004; Orchard et al., 2007; Peters et al., 2003). A central hypothesis explaining the neurologic benefit of allogeneic hematopoietic stem cell transplant is the penetration of donor-derived hematopoietic cells (most likely microglia) (Hess et al., 2004; Unger et al., 1993) into the central nervous system, where the missing enzyme is expressed by engrafted cells from which point the enzyme diffuses into CNS tissues and participates in clearing of storage materials. The level of enzyme provided to CNS tissues is thus limited to that amount expressed and released from donor-derived cells engrafting in the brain. While such engraftment is of great benefit for MPS I, recipients nonetheless continue to exhibit below normal IQ and impaired neurocognitive capability (Ziegler and Shapiro, 2007).

The phenomenon of metabolic cross correction also explains the effectiveness of ERT for several lysosomal storage diseases (Brady, 2006), most notably MPS I. However, due to the requirement for penetration of the blood-brain barrier (BBB) by the enzyme missing in the particular lysosomal storage disease (LSD) in order to effectively reach the CNS, effectiveness of enzyme therapy for neurologic manifestations of lysosomal storage disease (LSD) has not been observed (Brady, 2006). Enzymes are almost always too large and generally too charged to effectively cross the BBB. This has prompted investigations into invasive intrathecal enzyme administration (Dickson et al., 2007), for which effectiveness has been demonstrated in a canine model of MPS I (Kakkis et al., 2004) and for which human clinical trials are beginning for MPS I (Pastores, 2008; Munoz-Rojas et al., 2008). Key disadvantages of enzyme therapy include its great expense (>$200,000 per year) and the requirement for repeated infusions of recombinant protein. Current clinical trials of intrathecal IDUA administration are designed to inject the enzyme only once every three months, so the effectiveness of this dosing regimen remains uncertain.

SUMMARY OF THE INVENTION

Methods of preventing, inhibiting, and/or treating one or more symptoms associated with a disease of the central nervous system (CNS) in a mammal in need thereof are described. The methods involve delivering to the CNS of a mammal in need of treatment a composition comprising an effective amount of a recombinant adeno-associated virus (rAAV) vector comprising an open reading frame encoding a gene product, e.g., a therapeutic gene product. Target gene products that may be encoded by an rAAV vector include, but are not limited to, alpha-L-iduronidase, iduronate-2-sulfatase, heparan sulfate sulfatase, N-acetyl-alpha-D-glucosaminidase, beta-hexosaminidase, alpha-galactosidase, betagalactosidase, beta-glucuronidase or glucocerebrosidase. Diseases that may be prevented, inhibited or treated using the methods disclosed herein include, but are not limited to, mucopolysaccharidosis type I disorder, a mucopolysaccharidosis type II disorder, or a mucopolysaccharidosis type VII disorder. The AAV vector can be administered in a variety of ways to ensure that it is delivered to the CNS/brain, and that the transgene is successfully transduced in the subject's CNS/brain. Routes of delivery to the CNS/brain include, but are not limited to intrathecal administration, intracranial administration, e.g., intracerebroventricular administration, or lateral cerebro ventricular administration), intranasal administration, endovascular administration, and intraparenchymal administration.

In one embodiment, the methods involve delivering to the CNS of an adult mammal in need of treatment a composition comprising an effective amount of a rAAV-9 vector comprising an open reading frame encoding a gene. In one embodiment, the methods involve delivering to the CNS of an adult mammal in need of treatment a composition comprising an effective amount of a rAAV-9 vector comprising an open reading frame encoding IDUA. These methods are based, in part, on the discovery that an AAV-9 vector can efficiently transduce the therapeutic transgene in the brain/CNS of adult subjects, restoring enzyme levels to wild type levels. (see FIG. 15, infra). The results achieved using AAV-9 are surprising in view of previous work which demonstrated that intravascular delivery of AAV-9 in adult mice does not achieve widespread direct neuronal targeting (see Foust et al., 2009), as well as additional data showing that direct injection of AAV8-IDUA into the CNS of adult IDUA-deficient mice resulted in poor transgene expression (FIG. 18). As proof of principle, the working examples described herein use a pre-clinical model for the treatment of MPS1, an inherited metabolic disorder caused by deficiency of the lysosomal enzyme alpha-L-iduronidase (IDUA). The working examples surprisingly demonstrate that direct injection of AAV9-IDUA into the CNS of immunocompetent adult IDUA-deficient mice resulted in IDUA enzyme expression and activity that is the same or higher than IDUA enzyme expression and activity in wild-type adult mice (see FIG. 15, infra).

In an additional embodiment of the invention, the working examples also demonstrate that co-therapy to induce immunosuppression or immunotolerization, or treatment of immunodeficient animals, can achieve even higher levels of IDUA enzyme expression and activity. In an embodiment, patients with genotypes that promote an immune response that neutralizes enzyme activity (see, e.g., Barbier et al., 2013) are treated with an immunosuppressant in addition to the rAAV vector comprising an open reading frame encoding a gene product, such as IDUA.

Neonatal IDUA$^{-/-}$ mice are not immunocompetent. However administration of IDUA expressing AAV-8 to neonatal IDUA$^{-/-}$ mice resulted in IDUA expression (Wolf et al., 2011), thus tolerizing the animals to IDUA. As described herein, the applicability of AAV-mediated gene transfer to adult (immunocompetent) mice by direct infusion of AAV to the central nervous system was shown using different routes of administration. For example, AAV-IDUA serotype 9 was administered by direct injection into the lateral ventricles of adult IDUA-deficient mice that were either immunocompetent, immunodeficient (NODSCID/IDUA-/-), immunosuppressed with cyclophosphamide (CP), or immunotolerized by weekly injection of human iduronidase protein (Aldurazyme) starting at birth. CP immunosuppressed animals were also administered AAV9-IDUA by intranasal infusion, by intrathecal injection, and by endovascular infusion with and without mannitol to disrupt the blood-brain barrier. Animals were sacrificed at 8 weeks after vector administration, and brains were harvested and microdissected for evaluation of IDUA enzymatic activity, tissue glycosaminoglycans, and IDUA vector sequences in comparison with normal and affected control mice. Results from these studies show that numerous routes for AAV vector administration directly to the CNS may be employed, e.g., so as to achieve higher levels of protein delivery and/or enzyme activity in the CNS. In addition, although the brain is an immunopriviledged site, administration of an immunosuppressant or immunotolerization may increase the activity found in the brain after MV administration. Higher levels of expression per administration and/or less invasive routes of administration are clinically more palatable to patients.

Thus, the invention includes the use of recombinant AAV (rAAV) vectors that encode a gene product with therapeutic effects when expressed in the CNS of a mammal. In one embodiment, the mammal is an immunocompetent mammal with a disease or disorder of the CNS (a neurologic disease). An "immunocompetent" mammal as used herein is a mammal of an age where both cellular and humoral immune responses are elicited after exposure to an antigenic stimulus, by upregulation of Th1 functions or IFN-γ production in response to polyclonal stimuli, in contrast to a neonate which has innate immunity and immunity derived from the mother, e.g., during gestation or via lactation. An adult mammal that does not have an immunodeficiency disease is an example of an immunocompetent mammal. For example, an immunocompetent human is typically at least 1, 2, 3, 4, 5 or 6 months of age, and includes adult humans without an immunodeficiency disease. In one embodiment, the AAV is administered intrathecally. In one embodiment, the MV is administered intracranially (e.g., intracerebroventricularly). In one embodiment, the AAV is administered intranasally, with or without a permeation enhancer. In one embodiment, the AAV is administered endovascularly, e.g., carotid artery administration, with or without a permeation enhancer. In one embodiment, the mammal that is administered the AAV is immunodeficient or is subjected to immunotolerization or immune suppression, e.g., to induce higher levels of therapeutic protein expression relative to a corresponding mammal that is administered the MV but not subjected to immunotolerization or immune suppression. In one embodiment, an immune suppressive agent is administered to induce immune suppression. In one embodiment, the mammal that is administered the AAV is not subjected to immunotolerization or immune suppression (e.g., administration of the AAV alone provides for the therapeutic effect).

The invention provides a method to prevent, inhibit or treat one or more symptoms associated with a disease or disorder of the central nervous system in a mammal in need thereof. The method includes intrathecally, e.g., to the lumbar region, or intracerebroventricularly, e.g., to the lateral ventricle, administering to the mammal a composition comprising an effective amount of a rAAV vector comprising an open reading frame encoding a gene product, the expression of which in the central nervous system of the mammal prevents, inhibits or treats the one or more symptoms. In one embodiment, the gene product is a lysosomal storage enzyme. In one embodiment, the mammal is an immunocompetent adult. In one embodiment, the rAAV vector is an AAV-1, MV-2, AAV-3, AAV-4, AAV-5, AAV-6, AAV-7, AAV-8, MV rh10, or AAV-9 vector. In one embodiment, the mammal is a human. In one embodiment, multiple doses are administered. In one embodiment, the composition is administered weekly, monthly or two or more months apart.

In one embodiment, the method includes intrathecally, e.g., to the lumbar region, administering to a mammal a composition comprising an effective amount of a rAAV vector comprising an open reading frame encoding a gene product, the expression of which in the central nervous system of the mammal prevents, inhibits or treats the one or more symptoms, and optionally administering a permeation enhancer. In one embodiment, the permeation enhancer is administered before the composition. In one embodiment, the composition comprises a permeation enhancer. In one embodiment, the permeation enhancer is administered after the composition. In one embodiment, the gene product is a lysosomal storage enzyme. In one embodiment, the mammal is an immunocompetent adult. In one embodiment, the rAAV vector is an AAV-1, AAV-3, AAV-4, AAV-5, AAV-6, AAV-7, AAV-8, AAV rh10, or AAV-9 vector. In one embodiment, the mammal is a human. In one embodiment, multiple doses are administered. In one embodiment, the composition is administered weekly, monthly or two or more months apart. In one embodiment, the mammal that is intrathecally administered the AAV is not subjected to immunotolerization or immune suppression (e.g., administration of the AAV alone provides for the therapeutic effect). In one embodiment, the mammal that is intrathecally administered the AAV is immunodeficient or is subjected to immunotolerization or immune suppression, e.g., to induce higher levels of therapeutic protein expression relative to a corresponding mammal that is intrathecally administered the AAV but not subjected to immunotolerization or immune suppression.

In one embodiment, the method includes intracerebroventricularly, e.g., to the lateral ventricle, administering to an immunocompetent mammal a composition comprising an effective amount of a rAAV vector comprising an open reading frame encoding a gene product, the expression of which in the central nervous system of the mammal prevents, inhibits or treats the one or more symptoms. In one embodiment, the gene product is a lysosomal storage enzyme. In one embodiment, the rAAV vector is an AAV-1, AAV-2, AAV-3, AAV-4, AAV-5, MV-6, AAV-7, AAV rh10, or AAV-9 vector. In one embodiment, the rAAV vector is not a rAAV-5 vector. In one embodiment, the mammal is a human. In one embodiment, multiple doses are administered. In one embodiment, the composition is administered weekly, monthly or two or more months apart. In one embodiment, the mammal that is intracerebroventricularly administered the AAV is not subjected to immunotolerization or immune suppression (e.g., administration of the AAV alone provides for the therapeutic effect). In one embodiment, the mammal that is intracerebroventricularly administered the AAV is immunodeficient or is subjected to immunotolerization or immune suppression, e.g., to induce higher levels of therapeutic protein expression relative to a corresponding mammal that is intracerebroventricularly administered the AAV but not subjected to immunotolerization or immune suppression In one embodiment, the mammal is immunotolerized to the gene product before the composition comprising the AAV is administered.

Further provided is a method to prevent, inhibit or treat one or more symptoms associated with a disease or disorder of the central nervous system in a mammal in need thereof. The method includes endovascularly administering to the mammal a composition comprising an effective amount of a rAAV vector comprising an open reading frame encoding a gene product, the expression of which in the central nervous system of the mammal prevents, inhibits or treats the one or more symptoms, and an effective amount of a permeation enhancer. In one embodiment, the composition comprises the permeation enhancer. In one embodiment, the permeation enhancer comprises mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA. In one embodiment, the gene product is a lysosomal storage enzyme. In one embodiment, the mammal is an immunocompetent adult. In one embodiment, the rAAV vector is an AAV-1, AAV-2, AAV-3, AAV-4, AAV-5, AAV-6, AAV-7, AAV-8, MV rh10, or AAV-9 vector. In one embodiment, the rAAV vector is not a rAAV-5 vector. In one embodiment, the mammal is a human. In one embodiment, multiple doses are administered. In one embodiment, the composition is administered weekly. In one embodiment, the composition is administered weekly, monthly or two or more months apart. In one embodiment, the mammal that is endovascularly administered the AAV is not subjected to immunotolerization or immune suppression (e.g., administration of the MV provides for the therapeutic effect). In one embodiment, the mammal that is endovascularly administered the AAV is immunodeficient or is subjected to immunotolerization or immune suppression, e.g., to induce higher levels of therapeutic protein expression relative to a corresponding mammal that is endovascularly administered the AAV but not subjected to immunotolerization or immune suppression.

In one embodiment, the method includes intranasally administering to a mammal a composition comprising an effective amount of a rAAV-9 vector comprising an open reading frame encoding a gene product, the expression of which in the central nervous system of the mammal prevents, inhibits or treats the one or more symptoms, and optionally administering a permeation enhancer. In one embodiment, intranasal delivery may be accomplished as described in U.S. Pat. No. 8,609,088, the disclosure of which is incorporated by reference herein. In one embodiment, the permeation enhancer is administered before the composition. In one embodiment, the composition comprises a permeation enhancer. In one embodiment, the permeation enhancer is administered after the composition. In one embodiment, the gene product is a lysosomal storage enzyme. In one embodiment, the mammal is an immunocompetent adult. In one embodiment, the mammal is a human. In one embodiment, multiple doses are administered. In one embodiment, the composition is administered weekly, monthly or two or more months apart. In one embodiment, the mammal that is intranasally administered the AAV is not subjected to immunotolerization or immune suppression. In one embodiment, the mammal that is intranasally administered the AAV is subjected to immunotolerization or immune suppression, e.g., to induce higher levels of IDUA protein expression relative to a corresponding mammal that is intranasallly administered the AAV but not subjected to immunotolerization or immune suppression.

Also provided is a method to prevent, inhibit or treat one or more symptoms associated with a disease of the central nervous system in a mammal in need thereof. The method includes administering to the mammal a composition comprising an effective amount of a rAAV vector comprising an open reading frame encoding a gene product, the expression of which in the central nervous system of the mammal prevents, inhibits or treats the one or more symptoms, and an immune suppressant. In one embodiment, the immune suppressant comprises cyclophosphamide. In one embodiment, the immune suppressant comprises a glucocorticoid, cytostatic agents including an alkylating agent or an anti-metabolite such as methotrexate, azathioprine, mercaptopurine or a cytotoxic antibiotic, an antibody, or an agent active on immunophilin. In one embodiment, the immune suppressant comprises a nitrogen mustard, nitrosourea, a platinum compound, methotrexate, azathioprine, mercaptopurine, fluorouracil, dactinomycin, an anthracyclin, mitomycin C, bleomycin, mithramycin, IL2-receptor- (CD25-) or CD3- directed antibodies, anti-IL-2 antibodies, cyclosporin, tacrolimus, sirolimus, IFN-β, IFN-γ, an opioid, or TNF-α (tumor necrosis factor-alpha) binding agents such as infliximab (Remicade), etanercept (Enbrel), or adalimumab (Humira). In one embodiment, the rAAV and the immune suppressant are co-administered. In one embodiment, the rAAV is administered before and optionally after the immune suppressant. In one embodiment, the immune suppressant is administered before the rAAV. In one embodiment, the rAAV and the immune suppressant are intrathecally administered. In one embodiment, the rAAV and the immune suppressant are intracerebroventricularly administered. In one embodiment, the rAAV is intrathecally administered and the immune suppressant is intravenously administered. In one embodiment, the gene product is a lysosomal storage enzyme. In one embodiment, the mammal is an adult. In one embodiment, the rAAV vector is an AAV-1, AAV-2, AAV-3, AAV-4, AAV-5, AAV-6, AAV-7, AAV-8, AAV rh10, or AAV-9 vector. In one embodiment, the mammal is a human. In one embodiment, multiple doses are administered. In one embodiment, the composition is administered weekly. In one embodiment, the composition is administered weekly, monthly or two or more months apart.

The invention also provides a method to prevent, inhibit or treat one or more symptoms associated with a disease of the central nervous system in a mammal in need thereof. A mammal immunotolerized to a gene product that is associated with the disease is administered a composition comprising an effective amount of a rAAV vector comprising an open reading frame encoding a gene product, the expression of which in the central nervous system of the mammal prevents, inhibits or treats the one or more symptoms. In one embodiment, the gene product is a lysosomal storage enzyme. In one embodiment, the mammal is an adult. In one embodiment, the rAAV vector is an AAV-1, AAV-2, AAV-3, AAV-4, AAV-5, AAV-6, AAV-7, AAV-8, MV rh10, or AAV-9 vector. In one embodiment, the mammal is a human. In one embodiment, multiple doses are administered. In one embodiment, the composition is administered weekly.

Gene products that may be encoded by rAAV vectors include, but are not limited to, alpha-L-iduronidase, iduronate-2-sulfatase, heparan sulfate sulfatase, N-acetyl-alpha-D-glucosaminidase, beta-hexosaminidase, alpha-galactosidase, betagalactosidase, beta-glucuronidase, glucocerebrosidase, fibroblast growth factor-2 (FGF-2), brain derived growth factor (BDGF), neurturin, glial derived growth factor (GDGF), tyrosine hydroxylase, dopamine decarboxylase, or glutamic acid decarboxylase.

Diseases that have one or more neurologic symptoms that may be prevented, inhibited or treated using the methods disclosed herein include, but are not limited to, Adrenoleukodystrophy, Alzheimer disease, Amyotrophic lateral sclerosis, Angelman syndrome, Ataxia telangiectasia, Charcot-Marie-Tooth syndrome, Cockayne syndrome, Deafness, Duchenne muscular dystrophy, Epilepsy, Essential tremor, Fragile X syndrome, Friedreich's ataxia, Gaucher disease, Huntington disease, Lesch-Nyhan syndrome, Maple syrup urine disease, Menkes syndrome, Myotonic dystrophy, Narcolepsy, Neurofibromatosis, Niemann-Pick disease, Parkinson disease, Phenylketonuria, Prader-Willi syndrome, Refsum disease, Rett syndrome, Spinal muscular atrophy, Spinocerebellar ataxia, Tangier disease, Tay-Sachs disease, Tuberous sclerosis, Von Hippel-Lindau syndrome, Williams syndrome, Wilson's disease, or Zellweger syndrome. In one embodiment, the disease is a lysosomal storage disease, e.g., a lack or deficiency in a lysosomal storage enzyme. Lysosomal storage diseases include, but are not limited to, mucopolysaccharidosis (MPS) diseases, for instance, mucopolysaccharidosis type I, e.g., Hurler syndrome and the variants Scheie syndrome and Hurler-Scheie syndrome (a deficiency in alpha-L-iduronidase); Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV e.g., mucopolysaccharidosis type IV, e.g., Morquio syndrome (a deficiency of galactosamine-6-sulfate sulfatase or beta-galactosidase); mucopolysaccharidosis type VI, e.g., Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexosaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of a npc1 gene encoding a cholesterol metabolizing enzyme); Refsum disease; Sea-blue histiocyte disease; infantile sialic acid storage disorder; sialuria; multiple sulfatase deficiency; triglyceride storage disease with impaired long-chain fatty acid oxidation; Winchester disease; Wolman disease (a deficiency of cholesterol ester hydrolase); Deoxyribonuclease I-like 1 disorder; arylsulfatase E disorder; ATPase, H+ transporting, lysosomal, subunit 1 disorder; glycogen storage disease IIb; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria. Replacement of less than 20%, e.g., less than 10% or about 1% to 5% levels of lysosomal storage enzyme found in nondiseased mammals, may prevent, inhibit or treat neurological symptoms such as neurological degeneration in mammals.

In one embodiment, the methods described herein involve delivering to the CNS of an immunocompetent human in need of treatment a composition comprising an effective amount of a rAAV-9 vector comprising an open reading frame encoding a IDUA. Routes of administration to the CNS/brain include, but are not limited to intrathecal administration, intracranial administration, e.g., intracerebroventricular administration or lateral cerebro ventricular administration, intranasal administration, endovascular administration, and intraparenchymal administration.

Other viral vectors may be employed in the methods of the invention, e.g., viral vectors such as retrovirus, lentivirus, adenovirus, semliki forest virus or herpes simplex virus vectors.

BRIEF DESCRIPTION OF THE FIGURES

FIG. 1. Experimental design for iduronidase-deficient mice administered IDUA-AAV either intracerebroventricularly (ICV) or intrathecally. To prevent immune response, animals were either immunosuppressed with cyclophosphamide (CP), immunotolerized at birth by intravenous administration of human iduonidase protein (aldurazyme), or the injections were carried out in NOD-SCID immunodeficient mice that were also iduronidase deficient. Animals were sacrificed at the indicated time post-treatment, the brains were microdissected and extracts assayed for iduronidase activity.

FIG. 7. Data are grouped according the area of the brain.

FIG. 8. Assay for GAG storage material in the different sections of the brain for all four of the test groups.

FIG. 9. Schematic of experimental design.

FIG. 10. Intracranial infusion of AAV9IDUA into immunodeficient MPS I mice. Adult animals were injected with $10^{11}$ vector genomes and evaluated for iduronidase expression in the brain after 10 weeks. Enzyme activity levels in the brain were significantly higher than in the brains of wild type animals, and ranged from 30- to 300-fold higher than wild type.

FIG. 11. Intracranial administration of AAV9IDUA in immunocompetent, IDUA deficient mice. Adult animals were injected with $10^{11}$ vector genomes, and immunosuppressed by weekly injection of cyclophosphamide (CP). CP injections were terminated at 6 weeks post vector injection due to poor health, and the animals were sacrificed at 8 weeks post-injection. Brains were microdissected and assayed for IDUA enzyme activity.

FIG. 12. Intracranial infusion of AAV9IDUA into immunotolerized MPS I mice. MPS 1 mice were tolerized with either a single dose of Aldurazyme at birth or multiple doses administered weekly, starting at birth. Mice were infused with vector at 4 months, and sacrificed at 11 weeks after injection. Brains were microdissected and analyzed for iduronidase expression. Enzyme activities ranged from an average of 10- to 1000-fold higher than wild type levels.

FIG. 13. Intrathecal administration of AAV9IDUA in immunocompetent, IDUA deficient animals. Adult MPS I mice were injected with AAV9IDUA intrathecally, followed by a weekly immunosuppressive regimen of cyclophosphamide. Animals were sacrificed at 11 weeks post-injection, and then brains and spinal cords were analyzed for IDUA enzyme activity.

FIG. 14. Intrathecal infusion of AAV9IDUA in immunotolerized MPS I mice. IDUA deficient animals were tolerized at birth with a single dose of Aldurazyme or multiple doses administered weekly starting at birth. At 4 months of age animals were infused intrathecally with AAV9IDUA vector, and at 10 weeks post-injection animals were sacrificed, brains microdissected and assayed for iduronidase activity. There was restoration of enzyme activity in all parts of the brain, with activities in the cerebellum ranging from 200- to 1500-fold higher than wild type levels. Levels of enzyme activity in the olfactory bulb and cerebellum (to the right of the dashed line) correspond to the right Y-axis.

FIG. 15. Intrathecal infusion of AAV9IDUA in immunocompetent MPS I animals. Control MPS I animals were injected with AAV9IDUA vector, but were not immunosuppressed nor immunotolerized. Animals were sacrificed at 11 weeks after vector injection, and then their brains were assayed for iduronidase activity. Enzyme levels were restored to wild type levels in all parts of the brain, but were significantly lower than in animals that were either immunosuppressed or immunotolerized.

FIG. 16. Normalization of glycosaminoglycan (GAG) levels following intracranial or intrathecal AAV9 infusion. AAV9IDUA was injected intracranially or intrathecally into immunodeficient, immunosuppressed or immunotolerized MPS I mice as indicated. Animals were sacrificed 8-11 weeks after injection, then the brains were microdissected and analyzed for GAG levels. GAG storage was restored to wild type levels or close to wild type in all groups analyzed.

FIG. 17. IDUA vector copies in brain. Microdissected brains were analyzed for IDUA vector sequences by QPCR. The copy numbers in intracranially and intrathecally injected mice correlate to the levels of enzyme activity depicted in FIGS. 11 and 13.

FIG. 19. Intranasal administration of AAV9/IDUA in immunocompetent, IDUA deficient animals. Adult MPS I mice were infused with AAV9/IDUA intranasally, followed by a weekly immunosuppressive regimen of cyclophosphamide. Animals were sacrificed at 12 weeks post-injection and brains were analyzed for IDUA enzyme activity.

FIG. 20. IDUA vector copies in brain. Microdissected brains were analyzed for IDUA vector sequences by QPCR. The copy numbers in intranasally injected mice correlate to the levels of enzyme in FIG. 19.

DETAILED DESCRIPTION OF THE INVENTION

Definitions

Figure 2:
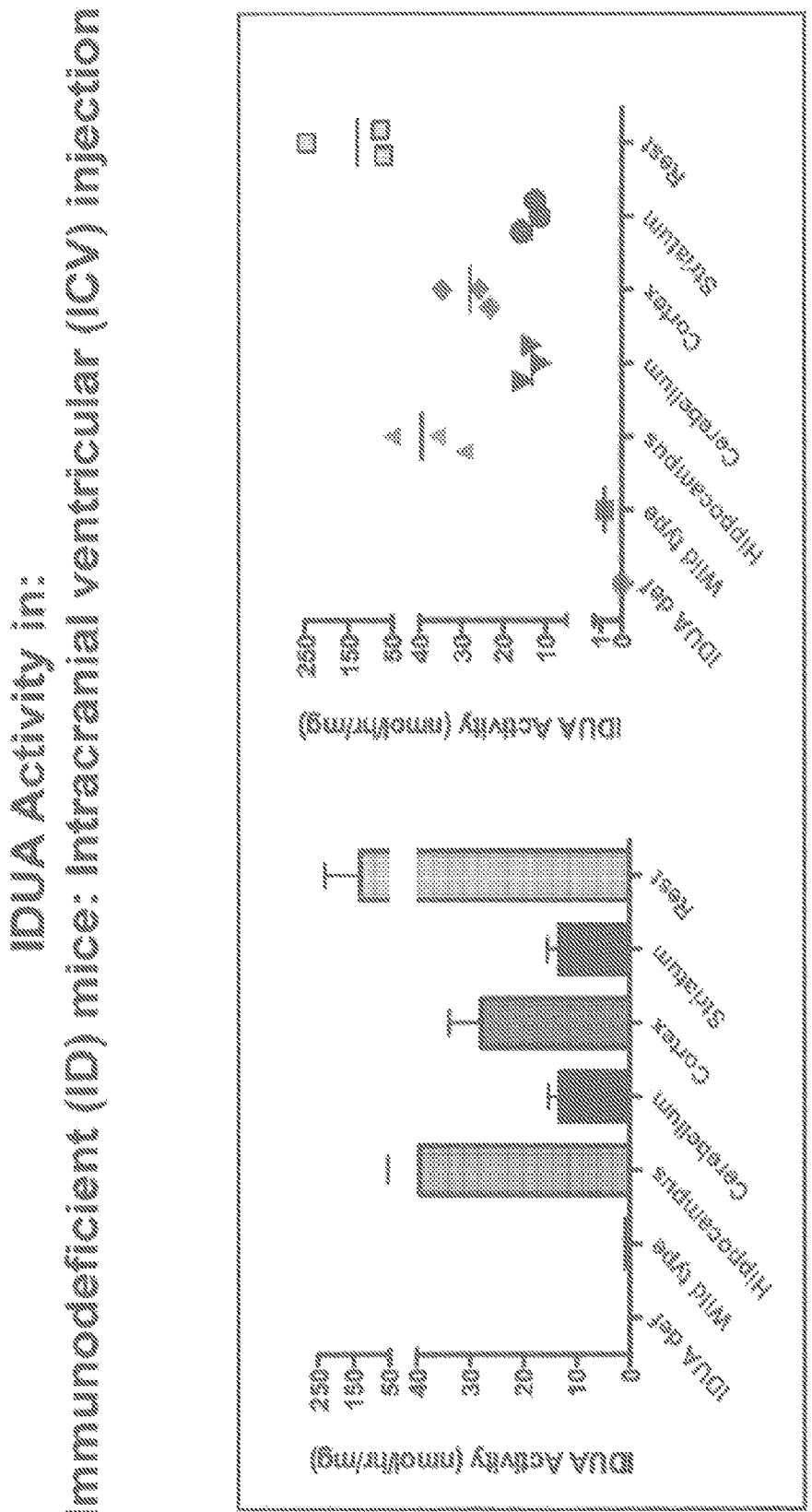
FIG. 2. IDUA activity in immunodeficient, IDUA deficient animals.

As used herein, "individual" (as in the subject of the treatment) means a mammal. Mammals include, for example, humans; non-human primates, e.g., apes and monkeys; and non-primates, e.g., dogs, cats, rats, mice, cattle, horses, sheep, and goats. Non-mammals include, for example, fish and birds.

The term "disease" or "disorder" are used interchangeably, and are used to refer to diseases or conditions wherein lack of or reduced amounts of a specific gene product, e.g., a lysosomal storage enzyme, plays a role in the disease such that a therapeutically beneficial effect can be achieved by supplementing, e.g., to at least 1% of normal levels.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, "inhibiting" means inhibition of further progression or worsening of the symptoms associated with the disorder or disease, and "preventing" refers to prevention of the symptoms associated with the disorder or disease.

As used herein, an "effective amount" or a "therapeutically effective amount" of an agent of the invention e.g., a recombinant AAV encoding a gene product, refers to an amount of the agent that alleviates, in whole or in part, symptoms associated with the disorder or condition, or halts or slows further progression or worsening of those symptoms, or prevents or provides prophylaxis for the disorder or condition, e.g., an amount that is effective to prevent, inhibit or treat in the individual one or more neurological symptoms.

In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest) and/or a selectable or detectable marker.

"AAV" is adeno-associated virus, and may be used to refer to the virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on its binding properties, e.g., there are eleven serotypes of AAVs, AAV-1-AAV-11, including AAV-2, AAV-5, AAV-8, AAV-9 and AAV rh10, and the term encompasses pseudotypes with the same binding properties. Thus, for example, AAV-5 serotypes include AAV with the binding properties of AAV-5, e.g., a pseudotyped AAV comprising AAV-5 capsid and a rAAV genome which is not derived or obtained from AAV-5 or which genome is chimeric. The abbreviation "rAAV" refers to recombinant adeno-associated virus, also referred to as a recombinant AAV vector (or "rAAV vector").

An "AAV virus" refers to a viral particle composed of at least one AAV capsid protein and an encapsidated polynucleotide. If the particle comprises a heterologous polynucleotide (i.e., a polynucleotide other than a wild-type AAV genome such as a transgene to be delivered to a mammalian cell), it is typically referred to as "rAAV". An MV "capsid protein" includes a capsid protein of a wild-type AAV, as well as modified forms of an AAV capsid protein which are structurally and or functionally capable of packaging a rAAV genome and bind to at least one specific cellular receptor which may be different than a receptor employed by wild type AAV. A modified AAV capsid protein includes a chimeric AAV capsid protein such as one having amino acid sequences from two or more serotypes of AAV, e.g., a capsid protein formed from a portion of the capsid protein from AAV-5 fused or linked to a portion of the capsid protein from AAV-2, and a AAV capsid protein having a tag or other detectable non-AAV capsid peptide or protein fused or linked to the AAV capsid protein, e.g., a portion of an antibody molecule which binds the transferrin receptor may be recombinantly fused to the AAV-2 capsid protein.

A "pseudotyped" rAAV is an infectious virus having any combination of an AAV capsid protein and an AAV genome. Capsid proteins from any AAV serotype may be employed with a rAAV genome which is derived or obtainable from a wild-type AAV genome of a different serotype or which is a chimeric genome, i.e., formed from AAV DNA from two or more different serotypes, e.g., a chimeric genome having 2 inverted terminal repeats (ITRs), each ITR from a different serotype or chimeric ITRs. The use of chimeric genomes such as those comprising ITRs from two AAV serotypes or chimeric ITRs can result in directional recombination which may further enhance the production of transcriptionally active intermolecular concatamers. Thus, the 5' and 3' ITRs within a rAAV vector of the invention may be homologous, i.e., from the same serotype, heterologous, i.e., from different serotypes, or chimeric, i.e., an ITR which has ITR sequences from more than one AAV serotype.

rAAV Vectors

Adeno-associated viruses of any serotype are suitable to prepare rAAV, since the various serotypes are functionally and structurally related, even at the genetic level. All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1 CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the MV rep gene with the putative helper-virus-inducible promoter (either known in the art or identified using well-known techniques such as linkage to promoter-less "reporter" genes). The AAV rep-cap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more AAV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

Pathways for Delivery

Despite the immense network of the cerebral vasculature, systemic delivery of therapeutics to the central nervous system (CNS) is not effective for greater than 98% of small molecules and for nearly 100% of large molecules (Partridge, 2005). The lack of effectiveness is due to the presence of the blood-brain barrier (BBB), which prevents most foreign substances, even many beneficial therapeutics, from entering the brain from the circulating blood. While certain small molecule, peptide, and protein therapeutics given systemically reach the brain parenchyma by crossing the BBB (Banks, 2008), generally high systemic doses are needed to achieve therapeutic levels, which can lead to adverse effects in the body. Therapeutics can be introduced directly into the CNS by intracerebroventricular or intraparenchymal injections. Intranasal delivery bypasses the BBB and targets therapeutics directly to the CNS utilizing pathways along olfactory and trigeminal nerves innervating the nasal passages (Frey I I, 2002; Thorne et al., 2004; Dhanda et al., 2005).

Any route of rAAV administration may be employed so long as that route and the amount administered are prophylactically or therapeutically useful. In one example, routes of administration to the CNS include intrathecal and intracranial. Intracranial administration may be to the cisterna *magna* or ventricle. The term "cisterna *magna*" is intended to include access to the space around and below the cerebellum via the opening between the skull and the top of the spine. The term "cerebral ventricle" is intended to include the cavities in the brain that are continuous with the central canal of the spinal cord. Intracranial administration is via injection or infusion and suitable dose ranges for intracranial administration are generally about $10^3$ to $10^{15}$ infectious units of viral vector per microliter delivered in 1 to 3000 microliters of single injection volume. For instance, viral genomes or infectious units of vector per micro liter would generally contain about $10^4$, $10^5$, $10^6$, $10^7$, $10^8$, $10^9$, $10^{10}$, $10^{11}$, $10^{12}$, $10^{13}$, or $10^{14}$ viral genomes or infectious units of viral vector delivered in about 10, 50, 100, 200, 500, 1000, or 2000 microliters. It should be understood that the aforementioned dosage is merely an exemplary dosage and those of skill in the art will understand that this dosage may be varied. Effective doses may be extrapolated from dose-responsive curves derived from in vitro or in vivo test systems.

The AAV delivered in the intrathecal methods of treatment of the present invention may be administered through any convenient route commonly used for intrathecal administration. For example, the intrathecal administration may be via a slow infusion of the formulation for about an hour. Intrathecal administration is via injection or infusion and suitable dose ranges for intrathecal administration are generally about $10^3$ to $10^{15}$ infectious units of viral vector per microliter delivered in, for example, 1 to 3000 microliters or 0.5 to 15 milliliters of single injection volume. For instance, viral genomes or infectious units of vector per microliter would generally contain about $10^4$, $10^5$, $10^6$, $10^7$, $10^8$, $10^9$, $10^{10}$, $10^{11}$, $10^{12}$, $10^{13}$, or $10^{14}$ viral genomes or infectious units of viral vector.

The therapy, if a lysosomal storage enzyme such as IDUA is expressed, results in the normalization of lysosomal storage granules in the neuronal and/or meningeal tissue of the subjects as discussed above. It is contemplated that the deposition of storage granules is ameliorated from neuronal and glial tissue, thereby alleviating the developmental delay and regression seen in individuals suffering with lysosomal storage disease. Other effects of the therapy may include the normalization of lysosomal storage granules in the cerebral meninges near the arachnoid granulation, the presence of which in lysosomal storage disease result in high pressure hydrocephalus. The methods of the invention also may be used in treating spinal cord compression that results from the presence of lysosomal storage granules in the cervical meninges near the cord at C1-C5 or elsewhere in the spinal cord. The methods of the invention also are directed to the treatment of cysts that are caused by the perivascular storage of lysosomal storage granules around the vessels of the brain. In other embodiments, the therapy also may advantageously result in normalization of liver volume and urinary glycosaminoglycan excretion, reduction in spleen size and apnea/hypopnea events, increase in height and growth velocity in prepubertal subjects, increase in shoulder flexion and elbow and knee extension, and reduction in tricuspid regurgitation or pulmonic regurgitation.

The intrathecal administration of the present invention may comprise introducing the composition into the lumbar area. Any such administration may be via a bolus injection. Depending on the severity of the symptoms and the responsiveness of the subject to the therapy, the bolus injection may be administered once per week, once per month, once every 6 months or annually. In other embodiments, the intrathecal administration is achieved by use of an infusion pump. Those of skill in the art are aware of devices that may be used to effect intrathecal administration of a composition. The composition may be intrathecally given, for example, by a single injection, or continuous infusion. It should be understood that the dosage treatment may be in the form of a single dose administration or multiple doses.

As used herein, the term "intrathecal administration" is intended to include delivering a pharmaceutical composition directly into the cerebrospinal fluid of a subject, by techniques including lateral cerebroventricular injection through a burrhole or cisternal or lumbar puncture or the like. The term "lumbar region" is intended to include the area between the third and fourth lumbar (lower back) vertebrae and, more inclusively, the L2-S1 region of the spine.

Administration of a composition in accordance with the present invention to any of the above mentioned sites can be achieved by direct injection of the composition or by the use of infusion pumps. For injection, the composition can be formulated in liquid solutions, e.g., y in physiologically compatible buffers such as Hank's solution, Ringer's solution or phosphate buffer. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the rAAV is administered by lateral cerebro-ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger, even though injection into the third and fourth smaller ventricles can also be made. In yet another embodiment, the compositions used in the present invention are administered by injection into the cisterna *magna* or lumbar area of a subject.

While the exact mechanisms underlying intranasal drug delivery to the CNS are not entirely understood, an accumulating body of evidence demonstrates that pathways involving nerves connecting the nasal passages to the brain and spinal cord are important. In addition, pathways involving the vasculature, cerebrospinal fluid, and lymphatic system have been implicated in the transport of molecules from the nasal cavity to the CNS. It is likely that a combination of these pathways is responsible, although one pathway may predominate, depending on the properties of the therapeutic, the characteristics of the formulation, and the delivery device used.

Therapeutics can rapidly gain access to the CNS following intranasal administration along olfactory nerve pathways leading from the nasal cavity directly to the CNS. Olfactory nerve pathways are a major component of intranasal delivery, evidenced by the fact that fluorescent tracers are associated with olfactory nerves as they traverse the cribriform plate (Jansson et al., 2002), drug concentrations in the olfactory bulbs are generally among the highest CNS concentrations observed (Thorne et al., 2004; Banks et al., 2004; Graff et al., 2005a); Nonaka et al., 2008; Ross et al., 2004; Ross et al., 2008; Thorne et al., 2008), and a strong, positive correlation exists between concentrations in the olfactory epithelium and olfactory bulbs (Dhuria et al., 2009a).

Olfactory pathways arise in the upper portion of the nasal passages, in the olfactory region, where olfactory receptor neurons (ORNs) are interspersed among supporting cells (sustentacular cells), microvillar cells, and basal cells. ORNs mediate the sense of smell by conveying sensory information from the peripheral environment to the CNS (Clerico et al., 2003). Beneath the epithelium, the lamina propria contains mucus secreting Bowman's glands, axons, blood vessels, lymphatic vessels, and connective tissue. The dendrites of ORNs extend into the mucous layer of the olfactory epithelium, while axons of these bipolar neurons extend centrally through the lamina propria and through perforations in the cribriform plate of the ethmoid bone, which separates the nasal and cranial cavities. The axons of ORNs pass through the subarachnoid space containing CSF and terminate on mitral cells in the olfactory bulbs. From there, neural projections extend to multiple brain regions including the olfactory tract, anterior olfactory nucleus, piriform cortex, amygdala, and hypothalamus (Buck, 2000). In addition to ORNs, chemosensory neurons located at the anterior tip of the nasal cavity in the Grueneberg ganglion lead into the olfactory bulbs (Fuss et al., 2005; Koos et al., 2005).

The unique characteristics of the ORNs contribute to a dynamic cellular environment critical for intranasal delivery to the CNS. Due to the direct contact with toxins in the external environment, ORNs regenerate every 3-4 weeks from basal cells residing in the olfactory epithelium (Mackay-Sim, 2003). Special Schwann cell-like cells called olfactory ensheathing cells (OECs) envelope the axons of ORNs and have an important role in axonal regeneration, regrowth, and remyelination (Field et al., 2003; Li et al., 2005a; Li et al., 2005b). The OECs create continuous, fluid-filled perineurial channels that, interestingly, remain open, despite the degeneration and regeneration of ORNs (Williams et al., 2004).

Given the unique environment of the olfactory epithelium, it is possible for intranasally administered therapeutics to reach the CNS via extracellular or intracellular mechanisms of transport along olfactory nerves. Extracellular transport mechanisms involve the rapid movement of molecules between cells in the nasal epithelium, requiring only several minutes to 30 minutes for a drug to reach the olfactory bulbs and other areas of the CNS after intranasal administration (Frey I I, 2002; Balin et al., 1986). Transport likely involves bulk flow mechanisms (Thorne et al., 2004; Thorne et al., 2001) within the channels created by the OECs. Drugs may also be propelled within these channels by the structural changes that occur during depolarization and axonal propagation of the action potential in adjacent axons (Luzzati et al., 2004). Intracellular transport mechanisms involve the uptake of molecules into ORNs by passive diffusion, receptor-mediated endocytosis or adsorptive endocytosis, followed by slower axonal transport, taking several hours to days for a drug to appear in the olfactory bulbs and other brain areas (Baker et al., 1986; Broadwell et al., 1985; Kristensson et al., 1971). Intracellular transport in ORNs has been demonstrated for small, lipophilic molecules such as gold particles (de Lorenzo, 1970; Gopinath et al., 1978), aluminum salts (Perl et al., 1987), and for substances with receptors on ORNs such as WGA-HRP (Thorne et al., 1995; Baker et al., 1986; Itaya et al., 1986; Shipley, 1985). Intracellular mechanisms, while important for certain therapeutics, are not likely to be the predominant mode of transport into the CNS. While some large molecules, such as galanin-like peptide (GALP), exhibit saturable transport pathways into the CNS (Nonaka et al., 2008), for other large molecules such as NGF and insulin-like growth factor-I (IGF-I), intranasal delivery into the brain is nonsaturable and not receptor mediated (Thorne et al., 2004; Chen et al., 1998; Zhao et al., 2004), An often overlooked but important pathway connecting the nasal passages to the CNS involves the trigeminal nerve, which innervates the respiratory and olfactory epithelium of the nasal passages and enters the CNS in the pons (Clerico et al., 2003; Graff et al., 2003). Interestingly, a small portion of the trigeminal nerve also terminates in the olfactory bulbs (Schaefer et al., 2002). The cellular composition of the respiratory region of the nasal passages is different from that of the olfactory region, with ciliated epithelial cells distributed among mucus secreting goblet cells. These cells contribute to mucociliary clearance mechanisms that remove mucus along with foreign substances from the nasal cavity to the nasopharynx. The trigeminal nerve conveys sensory information from the nasal cavity, the oral cavity, the eyelids, and the cornea, to the CNS via the ophthalmic division (V1), the maxillary division (V2), or the mandibular division (V3) of the trigeminal nerve (Clerico et al., 2003; Gray, 1978). Branches from the ophthalmic division of the trigeminal nerve provide innervation to the dorsal nasal mucosa and the anterior portion of the nose, while branches of the maxillary division provide innervation to the lateral walls of the nasal mucosa. The mandibular division of the trigeminal nerve extends to the lower jaw and teeth, with no direct neural inputs to the nasal cavity. The three branches of the trigeminal nerve come together at the trigeminal ganglion and extend centrally to enter the brain at the level of the pons, terminating in the spinal trigeminal nuclei in the brainstem. A unique feature of the trigeminal nerve is that it enters the brain from the respiratory epithelium of the nasal passages at two sites: (1) through the anterior lacerated foramen near the pons and (2) through the cribriform plate near the olfactory bulbs, creating entry points into both caudal and rostral brain areas following intranasal administration. It is also likely that other nerves that innervate the face and head, such as the facial nerve, or other sensory structures in the nasal cavity, such as the Grueneberg ganglion, may provide entry points for intranasally applied therapeutics into the CNS.

Traditionally, the intranasal route of administration has been utilized to deliver drugs to the systemic circulation via absorption into the capillary blood vessels underlying the nasal mucosa. The nasal mucosa is highly vascular, receiving its blood supply from branches of the maxillary, ophthalmic and facial arteries, which arise from the carotid artery (Clerico et al., 2003; Cauna, 1982). The olfactory mucosa receives blood from small branches of the ophthalmic artery, whereas the respiratory mucosa receives blood from a large caliber arterial branch of the maxillary artery (DeSesso, 1993). The relative density of blood vessels is greater in the respiratory mucosa compared to the olfactory mucosa, making the former region an ideal site for absorption into the blood (DeSesso, 1993). The vasculature in the respiratory region contains a mix of continuous and fenestrated endothelia (Grevers et al., 1987; Van Diest et al., 1979), allowing both small and large molecules to enter the systemic circulation following nasal administration.

Delivery to the CNS following absorption into the systemic circulation and subsequent transport across the BBB is possible, especially for small, lipophilic drugs, which more easily enter the blood stream and cross the BBB compared to large, hydrophilic therapeutics such as peptides and proteins.

Increasing evidence is emerging suggesting that mechanisms involving channels associated with blood vessels, or perivascular channels, are involved in intranasal drug delivery to the CNS. Perivascular spaces are bound by the outermost layer of blood vessels and the basement membrane of the surrounding tissue (Pollock et al., 1997). These perivascular spaces act as a lymphatic system for the brain, where neuron-derived substances are cleared from brain interstitial fluid by entering perivascular channels associated with cerebral blood vessels. Perivascular transport is due to bulk flow mechanisms, as opposed to diffusion alone (Cserr et al., 1981; Groothuis et al., 2007), and arterial pulsations are also a driving force for perivascular transport (Rennels et al., 1985; Rennels et al., 1985). Intranasally applied drugs can move into perivascular spaces in the nasal passages or after reaching the brain and the widespread distribution observed within the CNS could be due to perivascular transport mechanisms (Thorne et al., 2004).

Pathways connecting the subarachnoid space containing CSF, perineurial spaces encompassing olfactory nerves, and the nasal lymphatics are important for CSF drainage and these same pathways provide access for intranasally applied therapeutics to the CSF and other areas of the CNS. Several studies document that tracers injected into the CSF in the cerebral ventricles or subarachnoid space drain to the underside of the olfactory bulbs into channels associated with olfactory nerves traversing the cribriform plate and reach the nasal lymphatic system and cervical lymph nodes (Bradbury et al., 1983; Hatterer et al., 2006; Johnston et al., 2004a); Kida et al., 1993; Walter et al., 2006a; Walter et al., 2006b). Drugs can access the CNS via these same pathways after intranasal administration, moving from the nasal passages to the CSF to the brain interstitial spaces and perivascular spaces for distribution throughout the brain. These drainage pathways are significant in a number of animal species (sheep, rabbits, and rats) accounting for approximately 50% of CSF clearance (Bradbury et al., 1981; Boulton et al., 1999; Boulton et al., 1996; Cserr et al., 1992). Pathways between the nasal passages and the CSF are still important and functional in humans, evidenced by the fact that therapeutics are directly delivered to the CSF following intranasal delivery, without entering the blood to an appreciable extent (Born et al., 2002). A number of intranasal studies demonstrate that drugs gain direct access to the CSF from the nasal cavity, followed by subsequent distribution to the brain and spinal cord. Many intranasally applied molecules rapidly enter the CSF, and this transport is dependent on the lipophilicity, molecular weight, and degree of ionization of the molecules (Dhanda et al., 2005; Born et al., 2002; Kumar et al., 1974; Sakane et al., 1995; Sakane et al., 1994; Wang et al., 2007). Assessing distribution into the CSF can provide information on the mechanism of intranasal delivery.

Optimal delivery to the CNS along neural pathways is associated with delivery of the agent to the upper third of the nasal cavity (Hanson et al., 2008). Although a supine position may be employed another position for targeting the olfactory region is with the "praying to Mecca" position, with the head down-and-forward. A supine position with the head angle at 70° or 90° may be suitable for efficient delivery to the CSF using a tube inserted into the nostrils to deliver the drug via intranasal administration (van den Berg et al., (2002)).

For intranasal drug administration nose drops may be administered over a period of 10-20 minutes to alternating nostrils every 1-2 minutes to allow the solution to be absorbed into the nasal epithelium (Thorne et al., 2004; Capsoni et al., 2002; Ross et al., 2004; Ross et al., 2008; Dhuria et al., 2009a; Dhuria et al., 2009b; Francis et al., 2008; Martinez et al., 2008). This noninvasive method does not involve inserting the device into the nostril. Instead, drops are placed at the opening of the nostril, allowing the individual to sniff the drop into the nasal cavity. Other administration methods in anesthetized individual involve sealing the esophagus and inserting a breathing tube into the trachea to prevent the nasal formulation from being swallowed and to eliminate issues related to respiratory distress (Chow et al., 1999; Chow et al., 2001; Fliedner et al., 2006; Dahlin et al., 2001). Flexible tubing can be inserted into the nostrils for localized delivery of a small volume of the drug solution to the respiratory or olfactory epithelia, depending on the length of the tubing (Chow et al., 1999; Van den Berg et al., 2003; van den Berg et al., 2004a; Banks et al., 2004; van den Berg et al., 2002; Vyas et al., 2006a; Charlton et al., 2007a; Gao et al., 2007a).

Nasal delivery devices, such as sprays, nose droppers or needle-less syringes, may be employed to target the agent to different regions of the nasal cavity. OptiMist™ is a breath actuated device that targets liquid or powder nasal formulations to the nasal cavity, including the olfactory region, without deposition in the lungs or esophagus (Djupesland et al., 2006). The ViaNase™ device can also be used to target a nasal spray to the olfactory and respiratory epithelia of the nasal cavity. Nasal drops tend to deposit on the nasal floor and are subjected to rapid mucociliary clearance, while nasal sprays are distributed to the middle meatus of the nasal mucosa (Scheibe et al., 2008).

The immune suppressant or immunotolerizing agent may be administered by any route including parenterally. In one embodiment, the immune suppressant or immunotolerizing agent may be administered by subcutaneous, intramuscular, or intravenous injection, orally, intrathecally, intracranially, or intranasally, or by sustained release, e.g., using a subcutaneous implant. The immune suppressant or immunotolerizing agent may be dissolved or dispersed in a liquid carrier vehicle. For parenteral administration, the active material may be suitably admixed with an acceptable vehicle, e.g., of the vegetable oil variety such as peanut oil, cottonseed oil and the like. Other parenteral vehicles such as organic compositions using solketal, glycerol, formal, and aqueous parenteral formulations may also be used. For parenteral application by injection, compositions may comprise an aqueous solution of a water soluble pharmaceutically acceptable salt of the active acids according to the invention, desirably in a concentration of 0.01-10%, and optionally also a stabilizing agent and/or buffer substances in aqueous solution. Dosage units of the solution may advantageously be enclosed in ampules.

The composition, e.g., rAAV containing composition, immune suppressant containing composition or immunotolerizing composition, may be in the form of an injectable unit dose. Examples of carriers or diluents usable for preparing such injectable doses include diluents such as water, ethyl alcohol, macrogol, propylene glycol, ethoxylated isostearyl alcohol, polyoxyisostearyl alcohol and polyoxyethylene sorbitan fatty acid esters, pH adjusting agents or buffers such as sodium citrate, sodium acetate and sodium phosphate, stabilizers such as sodium pyrosulfite, EDTA, thioglycolic acid and thiolactic acid, isotonic agents such as sodium chloride and glucose, local anesthetics such as procaine hydrochloride and lidocaine hydrochloride. Furthermore usual solubilizing agents and analgesics may be added. Injections can be prepared by adding such carriers to the enzyme or other active, following procedures well known to those of skill in the art. A thorough discussion of pharmaceutically acceptable excipients is available in REMINGTON'S PHARMACEUTICAL SCIENCES (Mack Pub. Co., N.J. 1991). The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

When the immune suppressant or immunotolerizing agent is administered in the form of a subcutaneous implant, the compound is suspended or dissolved in a slowly dispersed material known to those skilled in the art, or administered in a device which slowly releases the active material through the use of a constant driving force such as an osmotic pump. In such cases, administration over an extended period of time is possible.

The dosage at which the immune suppressant or immunotolerizing agent containing composition is administered may vary within a wide range and will depend on various factors such as the severity of the disease, the age of the patient, etc., and may have to be individually adjusted. A possible range for the amount which may be administered per day is about 0.1 mg to about 2000 mg or about 1 mg to about 2000 mg. The compositions containing the immune suppressant or immunotolerizing agent may suitably be formulated so that they provide doses within these ranges, either as single dosage units or as multiple dosage units. In addition to containing an immune suppressant, the subject formulations may contain one or more rAAV encoding a therapeutic gene product.

Compositions described herein may be employed in combination with another medicament. The compositions can appear in conventional forms, for example, aerosols, solutions, suspensions, or topical applications, or in lyophilized form.

Typical compositions include a rAAV, an immune suppressant, a permeation enhancer, or a combination thereof, and a pharmaceutically acceptable excipient which can be a carrier or a diluent. For example, the active agent(s) may be mixed with a carrier, or diluted by a carrier, or enclosed within a carrier. When the active agent is mixed with a carrier, or when the carrier serves as a diluent, it can be solid, semi-solid, or liquid material that acts as a vehicle, excipient, or medium for the active agent. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active agent(s). Such additives can include wetting agents, emulsifying and suspending agents, salt for influencing osmotic pressure, buffers and/or coloring substances preserving agents, sweetening agents or flavoring agents. The compositions can also be sterilized if desired.

If a liquid carrier is used, the preparation can be in the form of a liquid such as an aqueous liquid suspension or solution. Acceptable solvents or vehicles include sterilized water, Ringer's solution, or an isotonic aqueous saline solution.

The agent(s) may be provided as a powder suitable for reconstitution with an appropriate solution as described above. Examples of these include, but are not limited to, freeze dried, rotary dried or spray dried powders, amorphous powders, granules, precipitates, or particulates. The composition can optionally contain stabilizers, pH modifiers, surfactants, bioavailability modifiers and combinations of these. A unit dosage form can be in individual containers or in multi-dose containers.

Compositions contemplated by the present invention may include, for example, micelles or liposomes, or some other encapsulated form, or can be administered in an extended release form to provide a prolonged storage and/or delivery effect, e.g., using biodegradable polymers, e.g., polylactide-polyglycolide. Examples of other biodegradable polymers include poly(orthoesters) and poly(anhydrides).

Polymeric nanoparticles, e.g., comprised of a hydrophobic core of polylactic acid (PLA) and a hydrophilic shell of methoxy-poly(ethylene glycol) (MPEG), may have improved solubility and targeting to the CNS. Regional differences in targeting between the microemulsion and nanoparticle formulations may be due to differences in particle size.

Liposomes are very simple structures consisting of one or more lipid bilayers of amphiphilic lipids, i.e., phospholipids or cholesterol. The lipophilic moiety of the bilayers is turned towards each other and creates an inner hydrophobic environment in the membrane. Liposomes are suitable drug carriers for some lipophilic drugs which can be associated with the non-polar parts of lipid bilayers if they fit in size and geometry. The size of liposomes varies from 20 nm to few μm.

Mixed micelles are efficient detergent structures which are composed of bile salts, phospholipids, tri, di- and mono-glycerides, fatty acids, free cholesterol and fat soluble micronutrients. As long-chain phospholipids are known to form bilayers when dispersed in water, the preferred phase of short chain analogues is the spherical micellar phase. A micellar solution is a thermodynamically stable system formed spontaneously in water and organic solvents. The interaction between micelles and hydrophobic/lipophilic drugs leads to the formation of mixed micelles (MM), often called swallen micelles, too. In the human body, they incorporate hydrophobic compounds with low aqueous solubility and act as a reservoir for products of digestion, e.g. monoglycerides.

Lipid microparticles includes lipid nano- and microspheres. Microspheres are generally defined as small spherical particles made of any material which are sized from about 0.2 to 100 μm. Smaller spheres below 200 nm are usually called nanospheres. Lipid microspheres are homogeneous oil/water microemulsions similar to commercially available fat emulsions, and are prepared by an intensive sonication procedure or high pressure emulsifying methods (grinding methods). The natural surfactant lecithin lowers the surface tension of the liquid, thus acting as an emulsifier to form a stable emulsion. The structure and composition of lipid nanospheres is similar to those of lipid microspheres, but with a smaller diameter.

Polymeric nanoparticles serve as carriers for a broad variety of ingredients. The active components may be either dissolved in the polymetric matrix or entrapped or adsorbed onto the particle surface. Polymers suitable for the preparation of organic nanoparticles include cellulose derivatives and polyesters such as poly(lactic acid), poly(glycolic acid) and their copolymer. Due to their small size, their large surface area/volume ratio and the possibility of functionalization of the interface, polymeric nanoparticles are ideal carrier and release systems. If the particle size is below 50 nm, they are no longer recognized as particles by many biological and also synthetic barrier layers, but act similar to molecularly disperse systems.

Thus, the composition of the invention can be formulated to provide quick, sustained, controlled, or delayed release, or any combination thereof, of the active agent after administration to the individual by employing procedures well known in the art. In one embodiment, the enzyme is in an isotonic or hypotonic solution. In one embodiment, for enzymes that are not water soluble, a lipid based delivery vehicle may be employed, e.g., a microemulsion such as that described in WO 2008/049588, the disclosure of which is incorporated by reference herein, or liposomes.

In one embodiment, the preparation can contain an agent, dissolved or suspended in a liquid carrier, such as an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens. For example, in addition to solubility, efficient delivery to the CNS following intranasal administration may be dependent on membrane permeability. For enzymes where paracellular transport is hindered due to size and polarity, improving membrane permeability may enhance extracellular mechanisms of transport to the CNS along olfactory and trigeminal nerves. One approach to modifying membrane permeability within the nasal epithelium is by using permeation enhancers, such as surfactants, e.g., lauroylcarnitine (LC), bile salts, lipids, cyclodextrins, polymers, or tight junction modifiers.

Generally, the active agents are dispensed in unit dosage form including the active ingredient together with a pharmaceutically acceptable carrier per unit dosage. Usually, dosage forms suitable for nasal administration include from about 125 μg to about 125 mg, e.g., from about 250 μg to about 50 mg, or from about 2.5 mg to about 25 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

The invention will be described by the following non-limiting examples.

EXAMPLE I

AAV Vector-Mediated Iduronidase Gene Delivery in a Murine Model of Mucopolysaccharidosis Type I: Comparing Different Routes of Delivery to the CNS Mucopolysaccharidosis type I (MPS I) is an inherited metabolic disorder caused by deficiency of the lysosomal enzyme alpha-L-iduronidase (IDUA). Systemic and abnormal accumulation of glycosaminoglycans is associated with growth delay, organomegaly, skeletal dysplasia, and cardiopulmonary disease. Individuals with the most severe form of the disease (Hurler syndrome) suffer from neurodegeneration, mental retardation, and early death. The two current treatments for MPS I (hematopoietic stem cell transplantation and enzyme replacement therapy) cannot effectively treat all central nervous system (CNS) manifestations of the disease.

Figure 18:
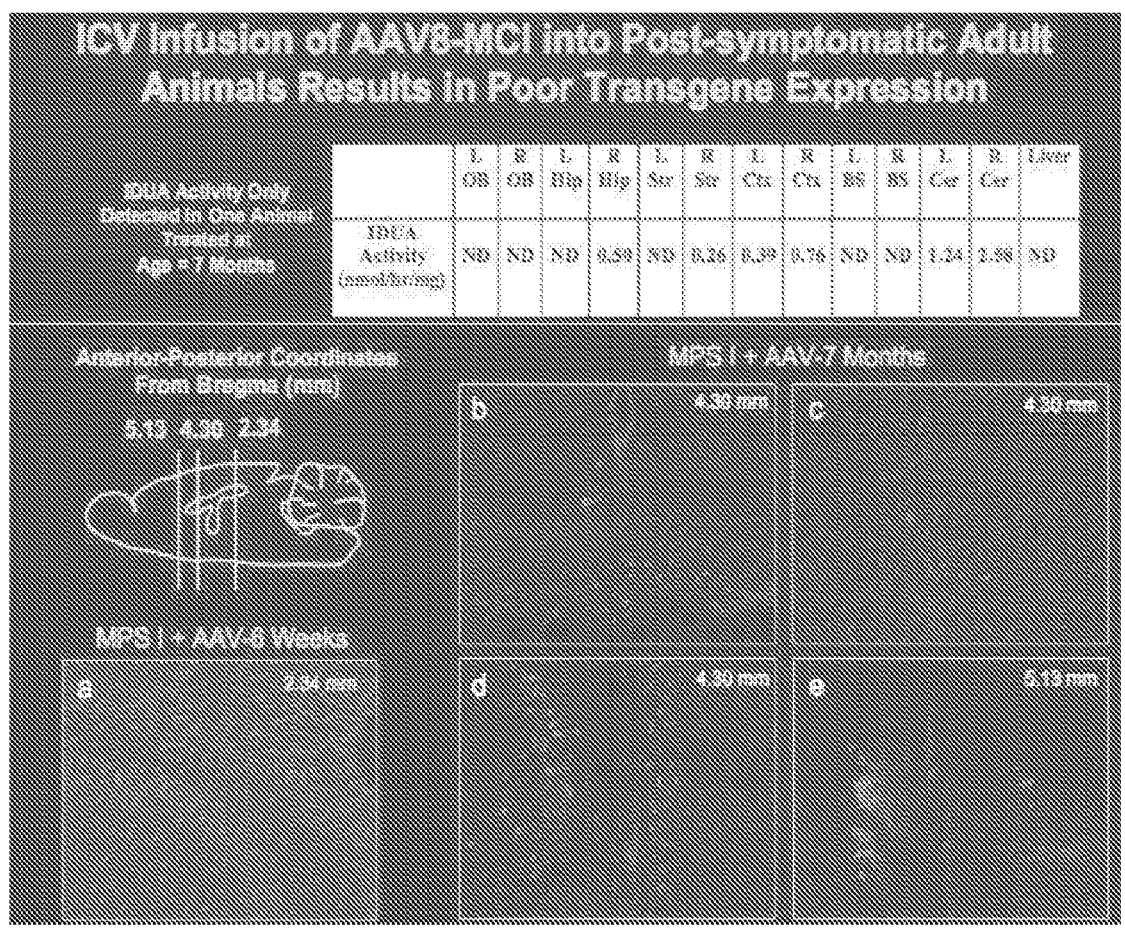
FIG. 18. ICV infusion of AAV8-MCI into adult animals.

With respect to gene therapy, it was previously demonstrated that intravascular delivery of AAV-9 in adult mice does not achieve widespread direct neuronal targeting (see Foust et al, 2009). Previous work also showed that direct injection of AAV8-IDUA into the CNS of adult IDUA-deficient mice resulted in a low frequency or a poor level of transgene expression (see FIG. 18). The following examples, which use a pre-clinical model for the treatment of MPS1, surprisingly demonstrate that direct injection of AAV9-IDUA into the CNS of immunocompetent adult IDUA-deficient mice resulted in IDUA enzyme expression and activity that is the same or higher than IDUA enzyme expression and activity in wild-type adult mice (see FIG. 15, infra).

Methods

AAV9-IDUA Preparation. The AAV-IDUA vector construct (MCI) has been previously described (Wolf et al., 2011) (mCags promoter). AAV-IDUA plasmid DNA was packaged into AAV9 virions at the University of Florida Vector Core, yielding a titer of $3 \times 10^{13}$ vector genomes per milliliter.

ICV Infusions. Adult Idua–/– mice were anesthetized using a cocktail of ketamine and xylazine (100 mg ketamine+10 mg xylazine per kg) and placed on a stereotactic frame. Ten microliters of AAV9-IDUA were infused into the right-side lateral ventricle (stereotactic coordinates AP 0.4, ML 0.8, DV 2.4 mm from bregma) using a Hamilton syringe. The animals were returned to their cages on heating pads for recovery.

Intrathecal Infusions. Infusions into young adult mice were carried out by injection of 10 μL AAV vector containing solution between the L5 and L6 vertebrae 20 minutes after intravenous injection of 0.2 mL 25% mannitol.

Immunotolerization. Newborn IDUA deficient mice were injected through the facial temporal vein with 5 μL containing 5.8 μg of recombinant iduronidase protein (Aldurazyme), and then the animals were returned to their cage.

Cyclophosphamide Immunosuppression. For immunosuppression, animals were administered cyclophosphamide once per week at a dose of 120 mg/kg starting one day after infusion with AAV9-IDUA vector.

Animals. Animals were anesthetized with ketamine/xylazine (100 mg ketamine+10 mg xylazine per kg) and transcardially perfused with 70 mL PBS prior to sacrifice. Brains were harvested and microdissected on ice into cerebellum, hippocampus, striatum, cortex, and brainstem/thalamus ("rest"). The samples were frozen on dry ice and then stored at –80° C. Samples were thawed and homogenized in 1 mL of PBS using a motorized pestle and permeabilized with 0.1% Triton X-100. IDUA activity was determined by fluorometric assay using 4MU-iduronide as the substrate. Activity is expressed in units (percent substrate converted to product per minute) per mg protein as determined by Bradford assay (BioRad).

Tissues. Tissue homogenates were clarified by centrifugation for 3 minutes at 13,000 rpm using an Eppendorf tabletop centrifuge model 5415D (Eppendorf) and incubated overnight with proteinase K, DNase1, and Rnase. GAG concentration was determined using the Blyscan Sulfated Glycosaminoglycan Assay (Accurate Chemical) according to the manufacturer's instructions.

Results

FIG. 1 shows the results for iduronidase-deficient mice that were administered AAV either intracerebroventricularly (ICV) or intrathecally (IT). To prevent immune response, animals were either immunosuppressed with cyclophosphamide (CP), immunotolerized at birth by intravenous administration of human iduonidase protein (aldurazyme), or the injections were carried out in NOD-SCID immunodeficient mice that were also iduronidase deficient. Animals were sacrificed at the indicated time post-treatment, the brains were microdissected and extracts assayed for iduronidase activity.

FIG. 2 illustrates data for immunodeficient, IDUA deficient animals injected ICV with AAV-IDUA vector. Those animals exhibited high levels of IDUA expression (10 to 100 times wild type) in all areas of the brain, with the highest level observed in the brain stem and thalamus ("rest").

Figure 3:
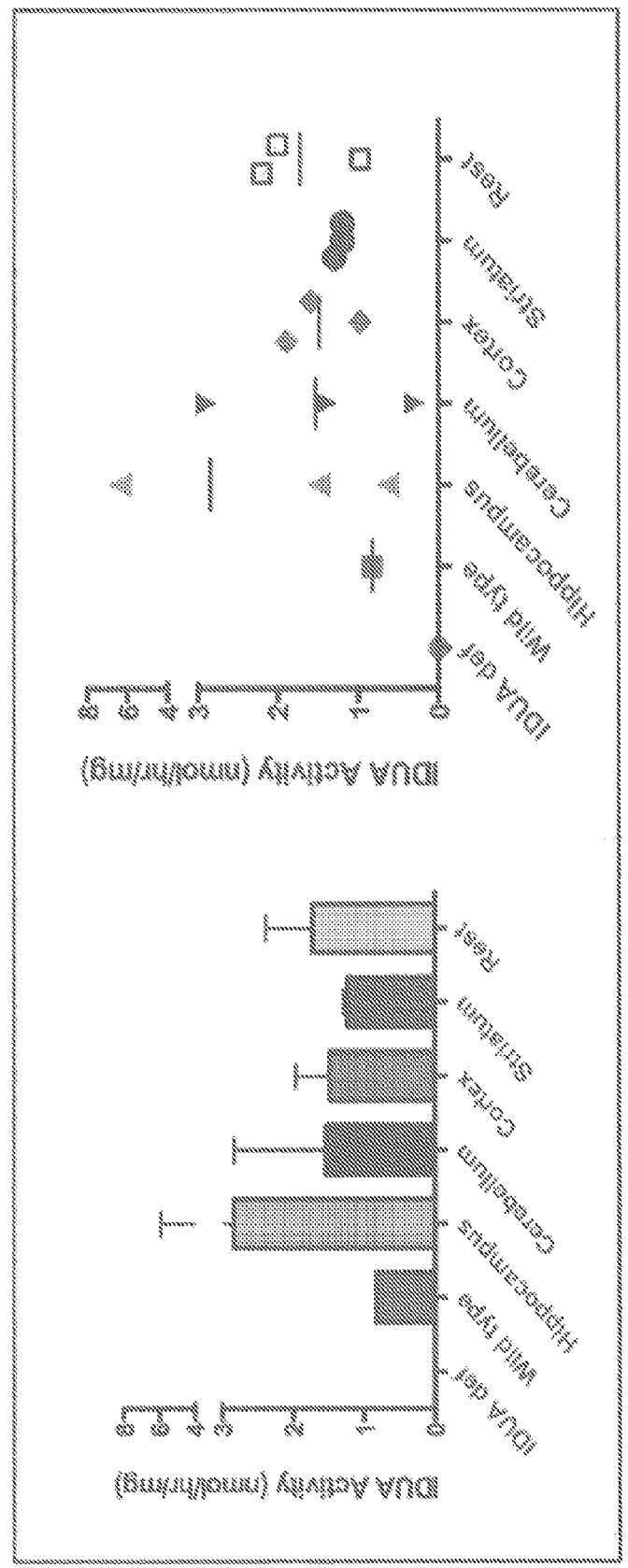
FIG. 3. IDUA activity in immunosuppressed animals administered AAV vector by ICV route.

Immunosuppressed animals administered AAV vector by ICV route had a relatively lower level of enzyme in the brain compared to the immunodeficient animals (FIG. 3). Note that immunosuppression may have been compromised in these animals because CP was withdrawn 2 weeks before sacrifice due to poor health.

Figure 4:
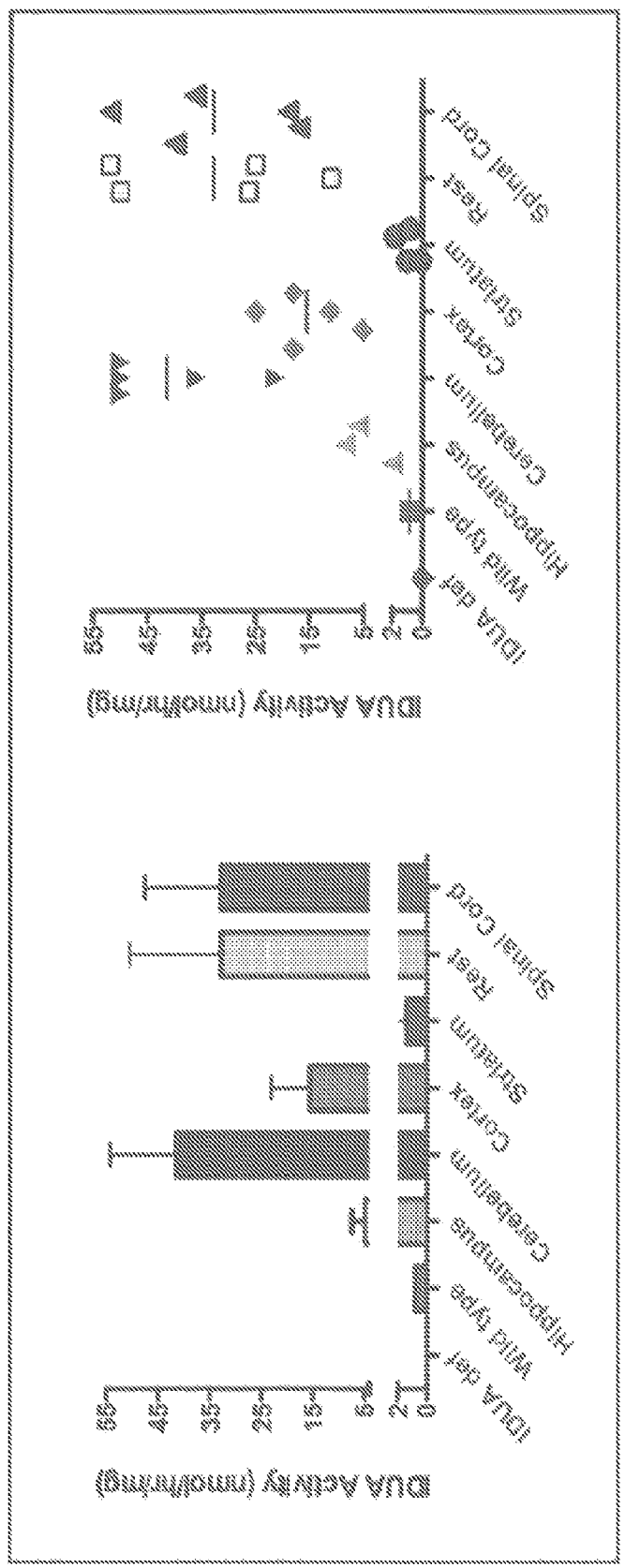
FIG. 4. IDUA activity in immunosuppressed animals administered AAV vector by IT route.
Figure 5:
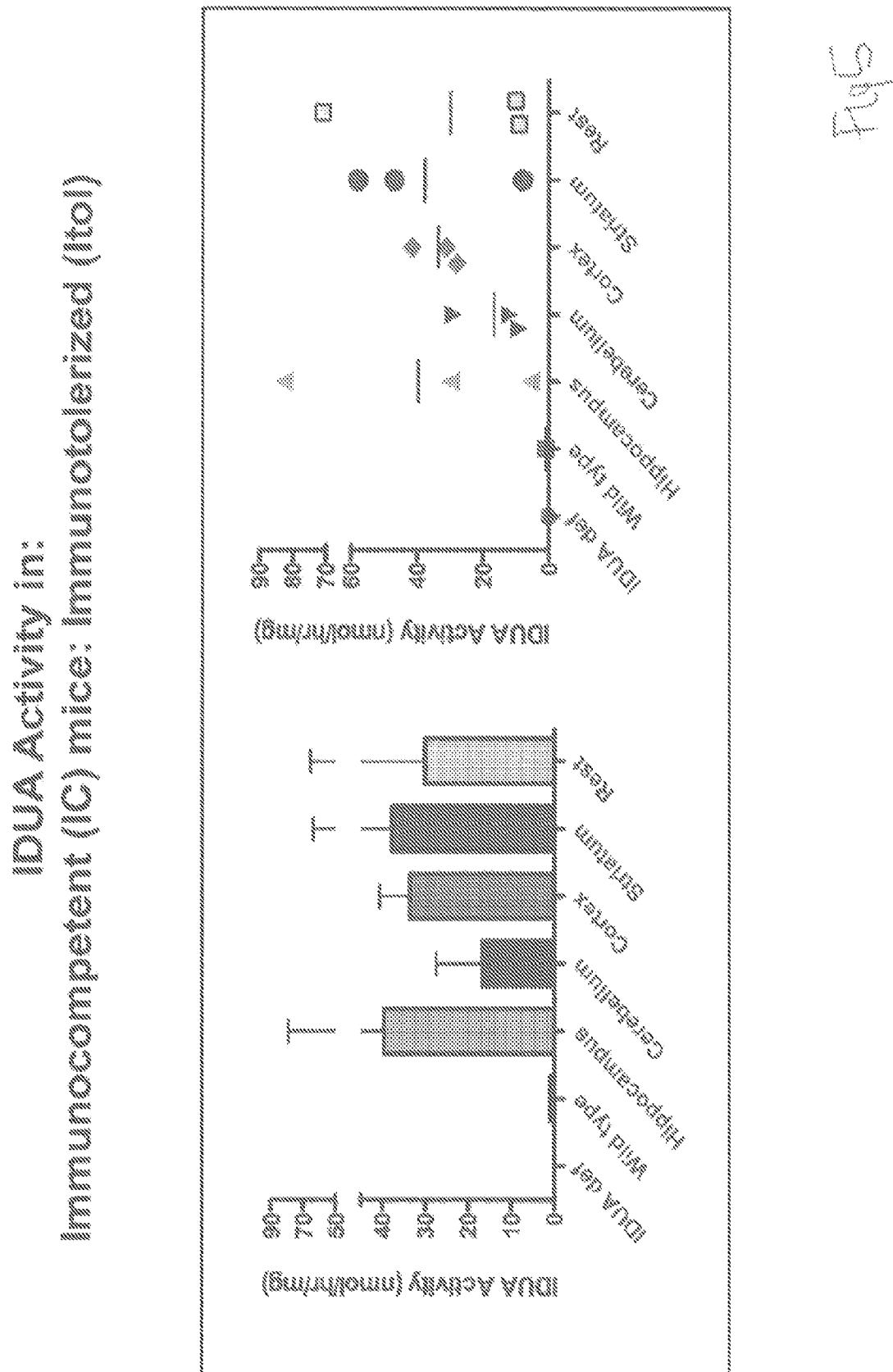
FIG. 5. IDUA activity in immunotolerized animals administered AAV vector ICV.

FIG. 4 shows data for immunosuppressed animals administered AAV vector by the IT route. Immunotolerized animals administered AAV vector ICV exhibited widespread IDUA activity in all parts of the brain (FIG. 5), similar to that observed in the immunodeficient animals, indicating the effectiveness of the immunotolerization procedure.

Figure 6:
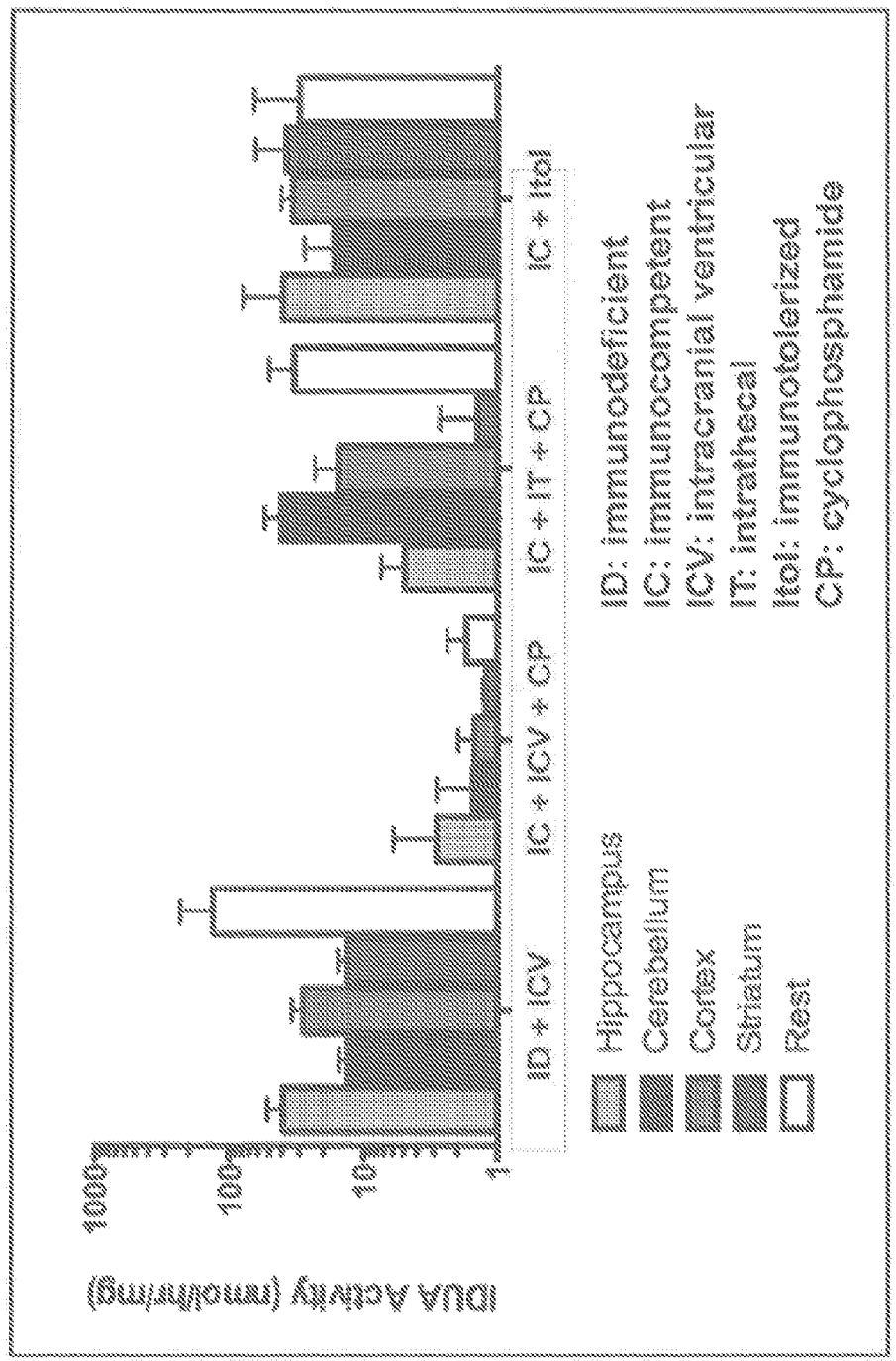
FIG. 6. Compilation of all mean levels of IDUA activity for side-by-side comparison.

FIG. 6 is a compilation of all mean levels of IDUA activity for side-by-side comparison, and FIG. 7 is data grouped according the area of the brain.

GAG storage material was assayed in the different sections of the brain for all four of the test groups. For each group, the mean of each portion of the brain is shown on the left, the values for each of the individual animals is shown on the right (FIG. 8). IDUA deficient animals (far left) contained high levels of GAG compared to wild type animals (magenta bar). GAG levels were at wild-type or lower than wild type for all portions of the brain in all groups of AAV-treated animals. GAG levels were slightly although not significantly higher than wild-type in cortex and brainstem of animals administered AAV9-IDUA intrathecally.

Conclusions

The results show high and widespread distribution of IDUA in the brain regardless of the route of delivery (ICV or IT) although IDUA expression in striatum and hippocampus was lower in animals injected IT versus ICV. There appears to be an immune response since immune deficient mice have higher levels of expression than immunocompetent mice. With regard to ICV injection, when CP was withdrawn early, IDUA expression is lower. In addition, immunotolerization was effective in restoring high levels of enzyme activity. Further, GAG levels were restored to normal in all treated experimental groups of mice.

EXAMPLE II

Methods

AAV9IDUA Preparation. AAV-IDUA plasmid was packaged into AAV9 virions at either the University of Florida vector core, or the University of Pennsylvania vector core, yielding a titer of $1-3 \times 10^{13}$ vector genomes per milliliter.

ICV Infusions. See Example I.

Intrathecal Infusions. See Example I.

Immunotolerization. As in Example I except: for multiple tolerizations, newborn IDUA deficient mice were injected with the first dose of Aldurazyme in the facial temporal vein, followed by 6 weekly injections administered intraperitoneally.

Cyclophosphamide Immunosuppression. See Example I.

Animals. Animals were anesthetized with ketamine/xylazine (100 mg ketamine+10 mg xylazine per kg) and transcardially perfused with 70 mL PBS prior to sacrifice. Brains were harvested and microdissected on ice into cerebellum, hippocampus, striatum, cortex, and brainstem/thalamus ("rest"). The samples were frozen on dry ice and then stored at –80° C.

Tissue IDUA Activity. Tissue samples were thawed and homogenized in saline in a tissue homogenizer. Tissue homogenates were clarified by centrifugation at 15,000 rpm in a benchtop Eppendorf centrifuge at 4° C. for 15 minutes.

Tissue lysates (supernatant) were collected and analyzed for IDUA activity and GAG storage levels.

Tissue GAG Levels. Tissue lysates were incubated overnight with Proteinase K, RNase and DNase. GAG levels were analyzed using the Blyscan Sulfated Glycosaminoglycan Assay according to the manufacturer's instructions.

IDUA Vector Copies. Tissue homogenates were used for DNA isolation and subsequent QPCR, as described in Wolf et al. (2011).

Results

FIG. 9 illustrates the experimental design and groups. Animals were administered AAV9IDUA vector either by intracerebroventricular (ICV) or intrathecal (IT) infusion. Vector administration was carried out in NOD-SCID immunodeficient (ID) mice that were also IDUA deficient, or in IDUA deficient mice that were either immunosuppressed with cyclophosphamide (CP), or immunotolerized at birth by a single or multiple injections of human iduronidase protein (Aldurazyme). The times of treatment with vector and sacrifice are as indicated in FIG. 9. All vector administrations were carried out in adult animals ranging in age from 3-4.5 months. Animals were injected with 10 µL of vector at a dose of $3 \times 10^{11}$ vector genomes per 10 microliters.

FIG. 10 shows IDUA enzyme activities in intracranially infused, immunodeficient, IDUA deficient mice. High levels of enzyme activity were seen in all areas of the brain, ranging from 30- to 300-fold higher than wild type levels. Highest enzyme expressions were seen in thalamus and brain stem, and in the hippocampus.

Animals that were injected intracranially and immunosuppressed with cyclophosphamide (CP) demonstrated significantly lower levels of enzyme activity than other groups (FIG. 11). However, CP administration in this case had to be withdrawn 2 weeks prior to sacrifice due to poor health of the animals.

IDUA enzyme levels in animals tolerized at birth with IDUA protein (Aldurazyme) and administered vector intracranially are depicted in FIG. 12. All animals showed high enzyme levels in all parts of the brain that ranged from 10- to 1000-fold higher than wild type levels, similar to levels achieved in immunodeficient animals, indicating the effectiveness of the immunotolerization procedure.

FIG. 13 depicts IDUA enzyme levels in mice that were injected intrathecally and administered CP on a weekly basis. Elevated levels of IDUA were observed in all parts of the brain, especially in the cerebellum and the spinal cord. Levels of enzyme were the lowest in the striatum and hippocampus with activities at wild type levels.

IDUA deficient mice were tolerized with Aldurazyme as described, and injected with vector intrathecally (FIG. 14). There was widespread IDUA enzyme activity in all parts of the brain, with highest levels of activity in the brain stem and thalamus, olfactory bulb, spinal cord and the cerebellum. Similar to the data in FIG. 13, the lowest levels of enzyme activity were seen in the striatum, cortex and hippocampus.

Control immunocompetent IDUA deficient animals were infused with vector intrathecally, without immunosuppression or immunotolerization (FIG. 15). The results indicate that although enzyme activities were at wild type levels or slightly higher, they are significantly lower than what was observed in animals that underwent immunomodulation. The decreases in enzyme levels were especially significant in the cerebellum, olfactory bulb and thalamus and brain stem, areas that expressed the highest levels of enzyme in immunomodulated animals.

Animals were assayed for GAG storage material, as shown in FIG. 15. All groups demonstrated clearance of GAG storage, with GAG levels similar to that observed in wild type animals. Animals that were immunosuppressed and injected with AAV-IDUA vector intrathecally had GAG levels in the cortex that were slightly higher than wild type, but still much lower than untreated IDUA deficient mice.

The presence of AAV9IDUA vector in animals that were immunotolerized and injected with vector either intracranially or intrathecally was evaluated by QPCR, as illustrated in FIG. 16. IDUA copies per cell were higher in animals infused intracranially in comparison with animals infused intrathecally, which is consistent with the higher level of enzyme activity seen in animals injected intracranially.

Conclusions

High, widespread, and therapeutic levels of IDUA were observed in all areas of the brain after intracerebroventricular and intrathecal routes of AAV9IDUA administration in adult mice. Enzyme activities were restored to wild type levels or slightly higher in immunocompetent IDUA deficient animals infused with AAV-IDUA intrathecally. Significantly higher levels of IDUA enzyme were observed for both routes of vector injection in animals immunotolerized starting at birth by administration of IDUA protein.

EXAMPLE III

Adult immunocompetent IDUA deficient mice (12 weeks old) were anesthetized with ketamine/xylazine, followed by intranasal infusion of AAV9IDUA vector. Vector was administered by applying eight 3 µL drops with a micropipette to the intranasal cavity, alternating between nostrils, at 2 minute intervals between each application. A total of $2.4-7 \times 10^{11}$ vector genomes was administered to each adult animal, depending on source of vector. Animals were immunosuppressed with 120 mg/kg cyclophosphamide administered weekly, starting the day after vector administration. Mice were sacrificed at 12 weeks post vector infusion, animals were assayed for IDUA enzyme expression and vector copies in the brain.

References

Al-Ghananeem et al., *AAPS Pharm. Sci. Tech.*, 3:E5 (2002).
Bagger et al., *Eur. J. Pharm. Sci.*, 21:235-242 (2004b).
Bagger et al., *Int. J. Pharm.*, 269:311-322 (2004a).
Baker et al., *Exp. Brain Res.*, 63:461 (1986).
Balin et al., *J. Comp. Neurol.*, 251:260-280 (1986).
Banks et al., *J. Drug Target*, 17:91-97 (2009).
Banks et al., *J. Pharmacol. Exp. Ther.*, 309:469 (2004).
Banks, *Biopolymers*, 90:589 (2008).
Barakat et al., *J. Pharm. Pharmacol.*, 58:63 (2006).
Barbier et al., *Mol. Genet. Metab.*, 110:303 (2013).
Baumgartner et al., *Neuron.*, 58:639 (2008).
Benedict et al., *Neuroendocrinology*, 86:136 (2007b).
Benedict et al., *Neuropsychopharmacology*, 32:239 (2007a).
Benedict et al., *Psychoneuroendocrinology*, 29:1326 (2004).
Bjoraker et al., *J. Dev. Behav. Ped.*, 27:290 (2006).
Blits et al., *J. Neuros. Methods*, 185:257 (2010).
Born et al., *Nat. Neurosci.*, 5:514 (2002).
Boulton et al., *Am. J. Physiol.*, 276:R818 (1999).
Boulton et al., *Neuropathol. Appl. Neurobiol.*, 22:325 (1996).
Bradbury et al., *Am. J. Physiol.*, 240:F329 (1981).
Bradbury et al., *J. Physiol.*, 339:519 (1983).
Brady, *Ann. Rev. Med.*, 57:283 (2006).
Broadwell et al., *J. Comp. Neurol.*, 242:632 (1985).
Broekman et al., *Neuroscience*, 138:501 (2006).
Buck, In: Kandel E R, Schwartz J H, Jessell T M, editors. Principles of neural science. 4th edition. New York: McGraw-Hill Companies. pp. 625-652 (2000).

Buxer et al., *J. Neurochem.*, 56:1012 (1991).
Cai et al., *Sichuan Da Xue Xue Bao Yi Xue Ban*, 39:438 (2008).
Capsoni et al., *Proc. Natl. Acad. Sci. USA*, 99:12432 (2002).
Carare et al., *Neuropathol. Appl. Neurobiol.*, 34:131 (2008).
Cauna, In: Proctor D F, Andersen I, editors. Amsterdam: Elsevier Biomedical Press. pp. 45-69 (1982).
Charlton et al., *Int. J. Pharm.*, 338:94 (2007b).
Charlton et al., *J. Drug Target*, 15:370 (2007a).
Charlton et al., *Pharm. Res.*, 25:1531 (2008).
Chen et al., *J. Alzheimers Dis.*, 1:35 (1998).
Chen et al., *J. Pharm. Sci.*, 95:1364 (2006).
Chow et al., *J. Pharm. Sci.*, 88:754 (1999).
Chow et al., *J. Pharm. Sci.*, 90:1729 (2001).
Clerico et al., In: Doty R L, editor. Handbook of olfaction and gustation. 2nd edition. New York: Marcel Dekker, Inc. pp. 1-16 (2003).
Costantino et al., *Int. J. Pharm.*, 337:1 (2007).
Cserr et al., *Am. J. Physiol.*, 240:F319 (1981).
Cserr et al., *Brain Pathol.*, 2:269 (1992).
Dahlin et al., *Eur. J. Pharm. Sci.*, 14:75 (2001).
Danhof et al., American Association of Pharmaceutical Scientists Annual Meeting, Atlanta, Ga. (2008).
Danielyan et al., *Eur. J. Cell. Biol.*, 88:315 (2009).
Davis et al., *Clin. Pharmacokinet.*, 42:1107 (2003).
de Lorenzo, In: Wolstenholme G E W, Knight J, editors. Taste and smell in vertebrates. London: Churchill. pp. 151-175 (1970).
De Rosa et al., *Proc. Natl. Acad. Sci. USA*, 102:3811 (2005).
DeSesso, *Qual. Assur.*, 2:213 (1993).
deSouza et al., *Eur. Neuropsychopharmacol.*, 19:53 (2009).
Dhanda et al., *Drug Del. Tech.*, 5:64 (2005).
Dhuria et al., *J. Pharm. Sci.*, 98:2501 (2009b).
Dhuria et al., *J. Pharmaceutical Sciences*, 99:1654 (2010).
Dhuria et al., *J. Pharmacol. Exp. Ther.*, 328:312 (2009a).
Diano et al., *J. Clin. Invest.*, 118:26 (2008).
Dickson et al., *Mol. Gen. Metab.*, 91:61 (2007).
Djupesland et al., *Laryngoscope*, 116:466 (2006).
Domes et al., *Biol. Psychiatry*, 61:731 (2007b).
Domes et al., *Biol. Psychiatry*, 62:1187 (2007a).
Dufes et al., *Int. J. Pharm.*, 255:87 (2003).
Einer-Jensen et al., *Exp. Brain Res.*, 130:216 (2000b).
Einer-Jensen et al., *Pharmacol. Toxicol.*, 87:276 (2000a).
Einer-Jensen et al., *Reproduction*, 129:9 (2005).
Ellinwood et al., *Mol. Genet. Metab.*, 91:239 (2007).
Fehm et al., *J. Clin. Endocrinol. Metab.*, 86:1144 (2001).
Field et al., *J. Neurocytol.*, 32:317 (2003).
Fliedner et al., *Endocrinology.*, 17:2088 (2006).
Foust et al., *Nat. Biotech.*, 27:5 (2009)).
Francis et al., *Brain*, 131:3311 (2008).
Fratantoni et al., *Science*, 162:570 (1968).
Frey et al., *Drug Delivery*, 4:87 (1997).
Frey I I, *Drug Del. Tech.*, 2:46 (2002).
Fuss et al., *Eur. J. Neurosci.*, 22:2649 (2005).
Gao et al., *Biomaterials*, 27:3482 (2006).
Gao et al., *Int. J. Pharm.*, 340:207 (2007a).
Gao et al., *J. Control Release*, 121:156 (2007b).
Gopinath et al., *Current Ther. Res.*, 23:596 (1978).
Gozes et al., *Curr. Alzheimer Res.*, 4:507 (2007).
Graff et al., *Pharm. Res.*, 20:1225 (2003).
Graff et al., *Pharm. Res.*, 22:235 (2005a).
Graff et al., *Pharm. Res.*, 22:86 (2005b).
Gray, 15th revised edition (Classic Collectors edition). New York: Bounty Books (1978).
Grevers et al., *Arch. Otorhinolaryngol.*, 244:55 (1987).
Groothuis et al., *J. Cereb. Blood Flow Metab.*, 27:43 (2007).
Gross et al., *J. Anat.*, 135:83 (1982).
Guastella et al., *Biol. Psychiatry*, 63:3 (2008).
Hadaczek et al., *Mol. Ther.*, 14:69 (2006).
Hallschmid et al., *Regul. Pept.*, 149:79 (2008).
Han et al., *J. Mol. Med.*, 85:75 (2007).
Hanson et al., *BMC Neurosci.*, 9:S5 (2008).
Hanson et al., *Drug Del. Tech.*, 4:66 (2004).
Hanson et al., San Diego, Calif.: Society for Neuroscience (2007).
Hanson et al., In: EPO, editor. Biopharm and HealthPartners Research Foundation (2008).
Hartung et al., *J. Am. Soc. Gene Ther.*, 9:866 (2004).
Hartung et al., *Mol. Thera.*, 9:869 (2004).
Hashizume et al., *Neuro. Oncol.*, 10:112 (2008).
Hatterer et al., *Blood*, 107:806 (2006).
Herati et al., *J. Gene Med.*, 10:972 (2008).
Hess et al., *Exp. Neuro.*, 186:134 (2004).
Horvat et al., *Eur. J. Pharm. Biopharm.*, 72:252 (2009).
Hussar et al., *Chem. Senses*, 27:7 (2002).
Illum, *J. Control Release*, 87:187 (2003).
Illum, *J. Pharm. Pharmacol.*, 56:3 (2004).
Itaya et al., *Brain Res.*, 398:397 (1986).
Jansson et al., *J. Drug Target*, 10:379 (2002).
Jogani et al., *Alzheimer Dis. Assoc. Disord.*, 22:116 (2008).
Johnston et al., *Cerebrospinal Fluid Res.*, 1:2 (2004).
Kakkis et al., *Mol. Gen. Met.*, 83:163 (2004).
Kandimalla et al., *J. Pharm. Sci.*, 94:613 (2005b).
Kandimalla et al., *Pharm. Res.*, 22:1121 (2005a).
Kida et al., *Neuropathol. Appl. Neurobiol.*, 19:480 (1993).
Kirsch et al., *J. Neurosci.*, 25:11489 (2005).
Klein et al., *J. Am. Soc. Gene Ther.*, 13:517 (2006).
Koos et al., *Neuroreport*, 16:1929 (2005).
Kosfeld et al., *Nature*, 435:673 (2005).
Kristensson et al., *Acta Neuropathol (Berl)*, 19:145 (1971).
Krivit, *Springer Seminars in Immunopathology*, 26:119 (2004).
Kumar et al., *Curr. Sci.*, 43:435 (1974).
Kumar et al., *Int. J. Pharm.*, 358:285 (2008).
Li et al., *Chin. J. Physiol.*, 48:7 (2005c).
Li et al., *Glia*, 52:245 (2005a).
Li et al., *J. Neurocytol.*, 34:343 (2005b).
Loftus et al., *Neuroscience*, 139:1061 (2006).
Luzzati et al., *J. Mol. Biol.*, 343:199 (2004).
Mackay-Sim, In: Doty R L, editor. Handbook of olfaction and gustation. 2nd edition. New York: Marcel Dekker, Inc. pp. 93-113 (2003).
Martinez et al., *Neuroscience*, 157:908 (2008).
Minn et al., *J. Drug Target*, 10:285 (2002).
Miragall et al., *J. Comp. Neurol.*, 341:433 (1994).
Muenzer, *J. Pediatrics*, 144:S27 (2004).
Munoz-Rojas et al., *Am. J. Med. Gen.*, 146A:2538 (2008).
Neufeld and Muenzer, In A. L. B. C. R. Scriver, W. S. Sly, et al (ed.), McGraw Hill, NY, pg. 3421 (2001).
Nonaka et al., *J. Pharmacol. Exp. Ther.*, 325:513 (2008).
Ohlfest et al., *Blood*, 105:2691 (2005).
Orchard et al., *J. Pediatrics*, 151:340 (2007).
Owens et al., *Diabet. Med.*, 20:886 (2003).
Pan et al., *Brain Res.*, 1188:241 (2008).
Pardridge, *NeuroRx*, 2:3 (2005).
Parker et al., *Psychoneuroendocrinology*, 30:924 (2005).
Pastores, *Exp. Opin. Biol. Ther.*, 8:1003 (2008).
Perl et al., *Lancet*, 1:1028 (1987).
Peters et al., *Bone Marrow Transpl.*, 31:229 (2003).
Pollock et al., *J. Anat.*, 191:337 (1997).
Raghavan et al., *J. Laryngol. Otol.*, 114:456 (2000).
Reger et al., *J. Alzheimers Dis.*, 13:323 (2008a).
Reger et al., *Neurobiol. Aging*, 27:451 (2006).
Reger et al., *Neurology*, 70:440 (2008b).

Rennels et al., *Adv. Neurol.*, 52:431 (1990).
Rennels et al., *Brain Res.*, 326:47 (1985).
Reolon et al., *Brain Res.*, 1076:225 (2006).
Rimmele et al., *J. Neurosci.*, 29:38 (2009).
Ross et al., *J. Neuroimmunol.*, 151:66 (2004).
Ross et al., *Neurosci. Lett.*, 439: 30 (2008).
Sakane et al., *J. Pharm. Pharmacol.*, 46:378 (1994).
Sakane et al., *J. Pharm. Pharmacol.*, 47:379 (1995).
Sarkar, *Pharm. Res.*, 9:1 (1992).
Schaefer et al., *J. Comp. Neurol.*, 444:221 (2002).
Scheibe et al., *Arch. Otolaryngol. Head Neck Surg.*, 134:643 (2008).
Schley et al., *J. Theor. Biol.*, 238:962 (2006).
Schulz et al., *Endocrinology*, 145:2696 (2004).
Scott et al., *Am. J. Hum. Genet.*, 53:973 (1993).
Shimizu et al., *Int. J. Obes. (Lond)*, 29:858 (2005).
Shipley, *Brain Res. Bull.*, 15:129 (1985).
Skipor et al., *Reprod. Biol.*, 3:143 (2003).
Steen et al., *J. Alzheimers Dis.*, 7:63 (2005).
Stefanczyk-Krzymowska et al., *Exp. Physiol.*, 85:801 (2000).
Takano et al., *J. Histochem. Cytochem.*, 53:611 (2005).
Thorne et al., *Brain Res.*, 692:278 (1995).
Thorne et al., *Clin. Pharmacokinet.*, 40:907 (2001).
Thorne et al., *Neuroscience*, 127:481 (2004).
Thorne et al., *Neuroscience*, 152:785 (2008).
Thorne, R G. 2002. The nasal pathways for drug delivery to the central nervous system: Studies with protein tracers and therapeutics. Doctoral Dissertation, University of Minnesota.
Unger et al., *J. Neuropath. Exp. Neuro.*, 52:460 (1993).
van den Berg et al., *Eur. J. Pharm. Biopharm.*, 58:131 (2004b).
Van den Berg et al., *J. Drug Target*, 11:325 (2003).
van den Berg et al., *J. Neurosci. Methods*, 116:99 (2002).
van den Berg et al., *Pharm. Res.*, 21:799 (2004a).
Van Diest et al., *J. Anat.*, 128:293 (1979).
Vyas et al., *AAPS PharmSciTech.*, 7:E1 (2006c).
Vyas et al., *Crit. Rev. Ther. Drug Carrier Syst.*, 23:319 (2006b).
Vyas et al., *J. Drug Target*, 13:317 (2005).
Vyas et al., *J. Pharm. Sci.*, 95:570 (2006a).
Walter et al., *Arch. Histol. Cytol.*, 69:37 (2006a).
Walter et al., *Neuropathol. Appl. Neurobiol.*, 32:388 (2006b).
Wang et al., *Cancer Chemother. Pharmacol.*, 57:97 (2006a).
Wang et al., *Eur. J. Pharm. Biopharm.*, 70:735 (2008).
Wang et al., *Int. J. Pharm.*, 317:40 (2006b).
Wang et al., *Int. J. Pharm.*, 341:20 (2007).
Watson et al., Gene Therapy, 16 Feb. 2006, doi:10.1038/sj.gt.3302735.
Weller et al., *Neurol. Res.*, 25:611 (2003).
Westin et al., *Eur. J. Pharm. Sci.*, 24:565 (2005).
Westin et al., *Pharm. Res.*, 23:565 (2006).
Williams et al., *J. Comp. Neurol.*, 470:50 (2004).
Wioland et al., *J. Histochem. Cytochem.*, 48:1215 (2000).
Wolf et al., *Neurobio. Dis.*, 43:123 (2011).
Xu et al., *J. Clin. Invest.*, 118:272 (2008).
Yamada et al., *Am. J. Physiol.*, 261:H1197 (1991).
Yang et al., *J. Pharm. Sci.*, 94:1577 (2005).
Zhang et al., *Acta Neuropathol. (Berl)*, 83:233 (1992).
Zhang et al., *Acta Pharmacol. Sin.*, 25:522 (2004a).
Zhang et al., *Int. J. Pharm.*, 275:85 (2004b).
Zhang et al., *J. Drug Target*, 14:281 (2006).
Zhao et al., *Acta Pharmacol. Sin.*, 28:273 (2007).
Zhao et al., *Chin. Med. Sci. J.*, 19:257 (2004).
Zheng et al., *Mol. Genet. Metab.*, 79:233 (2003).
Ziegler and Shapiro, In J. Donders and S. Hunter (ed.), Cambridge University Press, p. 427 (2007).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to inhibit or treat one or more symptoms of mucopolysaccharide type I (MPSI) in a mammal in need thereof, comprising:
    administering to a cisterna magna of the mammal in need thereof a composition comprising an amount of a recombinant adeno-associated virus (rAAV) 9 or rAAVrh10 vector comprising an open reading frame encoding alpha-L-iduronidase effective to inhibit or treat the one or more symptoms of MPSI.

2. The method of claim 1 wherein the mammal is an immunocompetent adult.

3. The method of claim 1 wherein the mammal is a human.

4. The method of claim 1 wherein neurodegeneration is inhibited or treated by the administration.

5. The method of claim 1 wherein prior to administration of the composition the mammal is immunotolerized to alpha-L-iduronidase.

6. The method of claim 1 wherein the amount administered reduces glycosaminoglycans (GAG).

7. The method of claim 1 wherein rAAV9 vector is administered.

8. The method of claim 1 wherein rAAVrh10 vector is administered.

9. A method to inhibit or treat one or more symptoms of mucopolysaccharidosis type I (MPSI) in a mammal in need thereof, comprising:
    administering to the mammal in need thereof an immune suppressant, and to a cisterna magna of the mammal a composition comprising an amount of a rAAV9 or rAAVrh10 vector comprising an open reading frame encoding alpha-L-iduronidase effective to inhibit or treat the one or more symptoms of MPSI.

10. The method of claim 9 wherein the immune suppressant comprises cyclophosphamide.

11. The method of claim 9 wherein the immune suppressant comprises a glucocorticoid, cytostatic agents including an alkylating agent, an anti-metabolite, a cytotoxic antibiotic, an antibody, or an agent active on immunophilin.

12. The method of claim 9 wherein the immune suppressant comprises a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent.

13. The method of claim 9 wherein the rAAV vector and the immune suppressant are co-administered or the immune suppressant is administered after the rAAV vector.

14. The method of claim 9 wherein the rAAV vector is a rAAV-9 vector.

15. The method of claim 9 wherein multiple doses of the composition comprising the rAAV9 or rAAVrh10 vector are administered.

16. The method of claim 9 wherein the rAAV vector is rAAVrh10 vector.

17. The method of claim 9 wherein the immune suppressant is administered before the rAAV9 or rAAVrh10 vector.

18. The method of claim 9 wherein the immune suppressant is systemically administered.

19. The method of claim 9 wherein the mammal is a human.

20. The method of claim 9 wherein the amount administered reduces glycosaminoglycans (GAG).

21. A method to inhibit or treat one or more symptoms associated with a deficiency in alpha-L-iduronidase (IDUA) in a mammal, comprising:
    providing a mammal with a deficiency in alpha-L-iduronidase that is immunotolerized to alpha-L-iduronidase ; and
    administering to a cisterna magna of the mammal a composition comprising an amount of a rAAV9 or rAAVrh10 vector comprising an open reading frame encoding alpha-L-iduronidase effective to inhibit or treat the one or more symptoms associated with the deficiency in alpha-L-iduronidase.

22. The method of claim 21 wherein multiple doses of the composition comprising the rAAV9 or rAAVrh10 vector are administered.

23. The method of claim 21 wherein rAAV9 vector is administered.

24. The method of claim 21 wherein rAAVrh10 vector is administered.

25. The method of claim 21 wherein the mammal is a human.

26. The method of claim 21 wherein the amount administered reduces glycosaminoglycans (GAG).

\* \* \* \* \*

UNITED STATES PATENT AND TRADEMARK OFFICE
CERTIFICATE OF CORRECTION

PATENT NO. : 9,827,295 B2
APPLICATION NO. : 14/889750
DATED : November 28, 2017
INVENTOR(S) : McIvor et al.

Page 1 of 2

It is certified that error appears in the above-identified patent and that said Letters Patent is hereby corrected as shown below:

On the Title Page

Item (54), in "Title", in Column 1, Line 2, delete "MUCOPOLYSACCHARIDE" and insert --MUCOPOLYSACCHARIDOSIS-- therefor On page 3, in Column 1, item (56), under "Other Publications", Line 62, delete "Pirimates"," and insert --Primates",-- therefor On page 3, in Column 2, item (56), under "Other Publications", Line 1, delete "adminstration" and insert --administration-- therefor On page 3, in Column 2, item (56), under "Other Publications", Line 27, delete "Adena-Associated" and insert --Adeno-Associated-- therefor On page 3, in Column 2, item (56), under "Other Publications", Line 40, delete "adena-associated" and insert --adeno-associated-- therefor On page 3, in Column 2, item (56), under "Other Publications", Line 51, delete "adena-associated" and insert --adeno-associated-- therefor On page 3, in Column 2, item (56), under "Other Publications", Line 59, delete "2014255417," and insert --2014265417,-- therefor In the Specification In Column 1, Line 2, delete "MUCOPOLYSACCHARIDE" and insert --MUCOPOLYSACCHARIDOSIS-- therefor In Column 4, Line 1, delete "MV" and insert --AAV-- therefor Signed and Sealed this
Fourth Day of June, 2019

Andrei Iancu
*Director of the United States Patent and Trademark Office*

CERTIFICATE OF CORRECTION (continued)
U.S. Pat. No. 9,827,295 B2

In Column 4, Line 22, delete "MV" and insert --AAV-- therefor

In Column 4, Line 32, delete "MV" and insert --AAV-- therefor

In Column 4, Line 52, delete "MV-2," and insert --AAV-2,-- therefor

In Column 4, Line 53, delete "MV" and insert --AAV-- therefor

In Column 5, Line 29, delete "MV-6," and insert --AAV-6,-- therefor

In Column 5, Line 67, delete "MV" and insert --AAV-- therefor

In Column 6, Line 8, delete "MV" and insert --AAV-- therefor

In Column 6, Line 42, delete "intranasallly" and insert --intranasally-- therefor In Column 6, Line 61, delete "anthracyclin," and insert --anthracycline,-- therefor In Column 7, Line 31, delete "MV" and insert --AAV-- therefor In Column 10, Line 40, delete "AAV9/IDUA" and insert --AAV9IDUA-- therefor In Column 10, Line 42, delete "AAV9/IDUA" and insert --AAV9IDUA-- therefor In Column 11, Line 64, delete "MV" and insert --AAV-- therefor In Column 12, Line 8, delete "MV-2," and insert --AAV-2,-- therefor In Column 14, Line 13, delete "MV" and insert --AAV-- therefor In Column 17, Line 5, delete "burrhole" and insert --burr hole-- therefor In Column 25, Line 39, delete "-80° C." and insert -- -80 °C.-- therefor In Column 26, Line 63, delete "-80° C." and insert -- -80 °C.-- therefor In the Claims In Column 32, Line 19, in Claim 1, delete "rAAVrh10vector" and insert --rAAVrh10 vector-- therefor In Column 32, Line 55, in Claim 12, delete "anthracyclin e," and insert --anthracycline,-- therefor In Column 33, Line 14, in Claim 21, delete "alpha-L-iduronidase ;" and insert --alpha-L-iduronidase;-- therefor